(12) United States Patent
Minamiguchi et al.

(10) Patent No.: US 7,884,934 B2
(45) Date of Patent: Feb. 8, 2011

(54) METHOD AND APPARATUS FOR BIOGENIC SUBSTANCE CONCENTRATION MEASUREMENT

(75) Inventors: Masaru Minamiguchi, Kyoto (JP); Tatsurou Kawamura, Kyoto (JP); Masahiko Shioi, Osaka (JP); Atsushi Matsubara, Osaka (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 12/828,775

(22) Filed: Jul. 1, 2010

(65) Prior Publication Data

US 2011/0001976 A1 Jan. 6, 2011

Related U.S. Application Data

(63) Continuation of application No. PCT/JP2009/007367, filed on Dec. 29, 2009.

(30) Foreign Application Priority Data

Apr. 14, 2009 (JP) .............................. 2009-097839
May 27, 2009 (JP) .............................. 2009-127343

(51) Int. Cl.
*G01J 4/00* (2006.01)
*G01N 21/00* (2006.01)

(52) U.S. Cl. ........................ 356/365; 356/436; 356/440

(58) Field of Classification Search ...................... None
See application file for complete search history.

(56) References Cited

U.S. PATENT DOCUMENTS 7,426,040 B2 * 9/2008 Kim et al. .................... 356/519

2008/0117423 A1 5/2008 Ogawa et al.
2008/0160287 A1 7/2008 Misawa et al.
2008/0316486 A1 12/2008 Nishiuma et al.
2009/0109422 A1 4/2009 Handa et al.
2010/0006774 A1 * 1/2010 Ohtsuka et al. .............. 356/246

FOREIGN PATENT DOCUMENTS

| JP | 2002-228662 | 8/2002 |
|---|---|---|
| JP | 2003-014765 | 1/2003 |
| JP | 3528800 | 5/2004 |
| JP | 2006-111675 | 4/2006 |
| JP | 2007-327948 | 12/2007 |
| JP | 2008-128893 | 6/2008 |
| JP | 2009-025295 | 2/2009 |
| WO | WO 2006/092963 A1 | 9/2006 |

* cited by examiner

*Primary Examiner*—Gregory J Toatley
*Assistant Examiner*—Juan D Valentin
(74) *Attorney, Agent, or Firm*—McDermott Will & Emery LLP

(57) ABSTRACT

The present invention provides an apparatus for biogenic substance concentration measurement including: a cell including therein a first region, a second region, and a test solution retention space; a light source; a polarizing plate; and a photoreceiver, in which a plurality of first metallic nanorods each having a first antibody on a surface thereof are immobilized on the first region, a plurality of second metallic nanorods each having a second antibody on a surface thereof are immobilized on the second region, the respective long axes of the plurality of first metallic nanorods are aligned in the same direction, the respective long axes of the plurality of second metallic nanorods are aligned in the same direction, the long-axis direction of the first metallic nanorod is orthogonal to the long-axis direction of the second metallic nanorod, and at least one of the polarizing plate and the cell is capable of rotation with an optical axis as the rotation axis.

45 Claims, 10 Drawing Sheets wavelength wavelength

US 7,884,934 B2

METHOD AND APPARATUS FOR BIOGENIC SUBSTANCE CONCENTRATION MEASUREMENT

BACKGROUND OF THE INVENTION

This Application is a continuation of International Application No. PCT/JP2009/007367, whose international filing date is Dec. 29, 2009, which in turn claims the benefit of Japanese Patent Application No. 2009-097839 filed on Apr. 14, 2009 and Japanese Patent Application No. 2009-127343 filed on May 27, 2009, the disclosures of which Applications are incorporated by reference herein. The benefit of the filing and priority dates of the International and Japanese Applications is respectfully requested.

TECHNICAL FIELD

The present invention relates to a method for biogenic substance concentration measurement and an apparatus therefor, with utilization of surface plasmon resonance.

BACKGROUND ART

Medical diagnosis, gene analysis, and the like are required to be conducted with promptness, high efficiency, and simplicity. Therefore recently, importance is given to a technology allowing highly-sensitive detection of a biogenic substance in very small amounts.

For example, surface plasmon resonance is utilized in a method for detecting biogenic substances such as proteins, hormones and low molecular weight compounds contained in test solutions of blood, perspiration, urine, or the like. Surface plasmon resonance occurs by free electrons in a metal interacting with electromagnetic waves (light). A detection method using surface plasmon resonance does not require labeling of the biogenic substance and is simple, differing from a fluorescence detection method and an electrochemical method.

Examples of surface plasmon resonance include propagating surface plasmon resonance and localized surface plasmon resonance.

A sensor using propagating surface plasmon resonance has, for example, a triangular prism. A thin metallic film is formed on one of the faces of the triangular prism. From a different face of the prism, light is radiated to the face having the thin metallic film. When light enters into the thin metallic film from a certain angle, propagating surface plasmon resonance occurs. This certain angle is referred to as the resonance angle. The resonance angle depends on the refractive index (permittivity) of a material that is present near the thin metallic film (about 100 nm). Therefore, the propagating surface plasmon resonance sensor can highly sensitively detect changes in property of a nearby material.

When propagating surface plasmon resonance is utilized in a biosensor, antibodies are immobilized on the surface of the thin metallic film. By bringing a test solution containing biogenic substances (antigens) into contact with the surface of the thin metallic film, the antigen and the antibody reacts with and bonds to each other. Since the refractive index near the thin metallic film changes, the resonance angle changes. If a correlation is obtained in advance between the concentration of antigens contained in the test solution and the resonance angle, the antigen concentration can be calculated from the change in the resonance angle.

On the other hand, localized surface plasmon resonance occurs by radiating light to particulates. Particulates such as metallic particulates and metal-coated dielectric particulates are used. The resonant wavelength in localized surface plasmon resonance depends on the refractive index of a material that is present near the particulates. Herein, "near" means, for example, a region within the length from the particulate surface to approximately the particulate radius, when the particulate is a spherical metallic particulate.

When localized surface plasmon resonance is utilized in a biosensor, antibodies are immobilized on the surface of a particulate. By bringing a test solution containing antigens into contact with the particulate, the antigen and the antibody react with and bond to each other. This causes change in the refractive index near the particulate. Therefore, the concentration of antigens contained in the test solution can be calculated by separating light transmitted through or reflected from the particulate, observing the spectrum, and then obtaining the resonant wavelength.

Patent Literature 1 discloses a biogenic substance detection apparatus that utilizes localized surface plasmon resonance. In Patent Literature 1, the substrate surface is divided into a plurality of regions. In each region, metal-coated dielectric particulates are formed. On the metal-coated dielectric particulate, antibodies that react with a biogenic substance are immobilized. Herein, the dielectric particulates formed on each detection region have different optical properties per detection region. Alternatively, different antibodies are immobilized per detection region. In this case, on each detection region, the biogenic substance differing per region reacts with and bonds to the antibody. By radiating light to each detection region, the respective resonant wavelengths reflecting the concentrations of the respective biogenic substances appear. In Patent Literature 1, a plurality of biogenic substances are detected by detecting the optical property of each detection region.

CITATION LIST

Patent Literature

[Patent Literature 1] Japanese Patent Publication No. 3528800

SUMMARY OF INVENTION

Technical Problem

In Patent Literature 1, a plurality of detection regions are provided on the substrate surface. This enables improved convenience, since multiple kinds of biogenic substances can be detected. However, since light is radiated to a plurality of detection regions, it is necessary to scan the light or to move the detection regions. Since the optical axis deviates during such scanning or movement, measurement accuracy can become low. In order to improve measurement accuracy, the positional relation of the light source, the detection regions, and the photoreceiver needs to be controlled with high accuracy. Thus, the apparatus according to Patent Literature 1 has a complex structure and is not suited for reducing size.

Simultaneously radiating light to each detection region can also be considered. However, it would become necessary to provide a plurality of optical axes or to broaden the target regions for the radiation.

Solution to Problem

The present invention provides a method for measuring respective concentrations of a first antigen and a second antigen contained in a test solution by using an apparatus for biogenic substance concentration measurement, having the steps of:

preparing the apparatus for biogenic substance concentration measurement, the apparatus comprising: a cell comprising therein a first region, a second region, and a test solution retention space; a light source; a polarizing plate for polarizing light radiated from the light source; and a photoreceiver for receiving light transmitted through the cell along an optical axis intersecting with the first region, the second region, and the test solution retention space, in which a plurality of first metallic nanorods each having a first antibody on a surface thereof are immobilized on the first region, a plurality of second metallic nanorods each having a second antibody on a surface thereof are immobilized on the second region, the respective long axes of the plurality of first metallic nanorods are aligned in the same direction, the respective long axes of the plurality of second metallic nanorods are aligned in the same direction, the long-axis direction of the first metallic nanorod is orthogonal to the long-axis direction of the second metallic nanorod, and at least one of the polarizing plate and the cell is capable of rotation with the optical axis as the rotation axis, supplying the test solution to the test solution retention space to allow the first antigen and the second antigen to react with the first antibody and the second antibody, respectively, transmitting along the optical axis a polarized light parallel to the long-axis direction of the plurality of first metallic nanorods to receive with the photoreceiver a first light thus obtained, rotating at least one of the polarizing plate and the cell to set a polarized light transmitted through the polarizing plate to be parallel to the long-axis direction of the plurality of second metallic nanorods, transmitting along the optical axis the polarized light parallel to the long-axis direction of the plurality of second metallic nanorods to receive with the photoreceiver a second light thus obtained, and calculating the respective concentrations of the first antigen and the second antigen based respectively on the first light and the second light.

Further, the present invention provides a method for measuring respective concentrations of a first antigen and a second antigen contained in a test solution by using an apparatus for biogenic substance concentration measurement, having the steps of:

preparing the apparatus for biogenic substance concentration measurement, the apparatus comprising: a cell comprising therein a first region, a second region, and a test solution retention space; a light source for radiating polarized light to the cell; and a photoreceiver for receiving light transmitted through the cell along an optical axis intersecting with the first region, the second region, and the test solution retention space, in which a plurality of first metallic nanorods each having a first antibody on a surface thereof are immobilized on the first region, a plurality of second metallic nanorods each having a second antibody on a surface thereof are immobilized on the second region, the respective long axes of the plurality of first metallic nanorods are aligned in the same direction, the respective long axes of the plurality of second metallic nanorods are aligned in the same direction, the long-axis direction of the first metallic nanorod is orthogonal to the long-axis direction of the second metallic nanorod, and at least one of the light source and the cell is capable of rotation with the optical axis as the rotation axis, supplying the test solution to the test solution retention space to allow the first antigen and the second antigen to react with the first antibody and the second antibody, respectively, transmitting along the optical axis a polarized light parallel to the long-axis direction of the plurality of first metallic nanorods to receive with the photoreceiver a first light thus obtained, rotating at least one of the light source and the cell to set a polarized light radiated from the light source to be parallel to the long-axis direction of the plurality of second metallic nanorods, transmitting along the optical axis the polarized light parallel to the long-axis direction of the plurality of second metallic nanorods to receive with the photoreceiver a second light thus obtained, and calculating the respective concentrations of the first antigen and the second antigen based respectively on the first light and the second light.

Still further, the present invention provides a method for measuring respective concentrations of a first antigen and a second antigen contained in a test solution by using a cell, having the steps of:

preparing the cell, the cell comprising therein a first region, a second region, and a test solution retention space; in which a plurality of first metallic nanorods each having a first antibody on a surface thereof are immobilized on the first region, a plurality of second metallic nanorods each having a second antibody on a surface thereof are immobilized on the second region, the respective long axes of the plurality of first metallic nanorods are aligned in the same direction, the respective long axes of the plurality of second metallic nanorods are aligned in the same direction, and the long-axis direction of the first metallic nanorod is orthogonal to the long-axis direction of the second metallic nanorod;

supplying the test solution to the test solution retention space to allow the first antigen and the second antigen to react with the first antibody and the second antibody, respectively;

transmitting through the cell along an optical axis intersecting with the first region, the second region, and the test solution retention space, a polarized light parallel to the long-axis direction of the plurality of first metallic nanorods to obtain a first light;

transmitting through the cell along the optical axis, a polarized light parallel to the long-axis direction of the plurality of second metallic nanorods to obtain a second light; and calculating the respective concentrations of the first antigen and the second antigen based respectively on the first light and the second light.

The present invention provides an apparatus for biogenic substance concentration measurement, comprising: a cell comprising therein a first region, a second region, and a test solution retention space; a light source; a polarizing plate for polarizing light radiated from the light source; and a photoreceiver for receiving light transmitted through the cell along an optical axis intersecting with the first region, the second region, and the test solution retention space, in which a plurality of first metallic nanorods each having a first antibody on a surface thereof are immobilized on the first region, a plurality of second metallic nanorods each having a second antibody on a surface thereof are immobilized on the second region, the respective long axes of the plurality of first metallic nanorods are aligned in the same direction, the respective long axes of the plurality of second metallic nanorods are aligned in the same direction, the long-axis direction of the first metallic nanorod is orthogonal to the long-axis direction of the second metallic nanorod, and at least one of the polarizing plate and the cell is capable of rotation with the optical axis as the rotation axis.

Further, the present invention provides an apparatus for biogenic substance concentration measurement, comprising: a cell comprising therein a first region, a second region, and a test solution retention space; a light source for radiating polarized light to the cell; and a photoreceiver for receiving light transmitted through the cell along an optical axis intersecting with the first region, the second region, and the test solution retention space, in which a plurality of first metallic nanorods each having a first antibody on a surface thereof are immobilized on the first region, a plurality of second metallic nanorods each having a second antibody on a surface thereof are immobilized on the second region, the respective long axes of the plurality of first metallic nanorods are aligned in the same direction, the respective long axes of the plurality of second metallic nanorods are aligned in the same direction, the long-axis direction of the first metallic nanorod is orthogonal to the long-axis direction of the second metallic nanorod, and at least one of the light source and the cell is capable of rotation with the optical axis as the rotation axis.

In one embodiment of the present invention, the cell comprises a first substrate and a second substrate. The first substrate has the first region on one surface thereof, and the second substrate has the second region on one surface thereof.

In one embodiment of the present invention, the first region and the second region face the same direction.

In the present embodiment, a first spacer is disposed around the first region, and a cover is disposed correspondingly to the first substrate with the first spacer interposed therebetween. The first region, the first spacer, and the cover form a first space. A second spacer is disposed around the second region. The other face of the first substrate, the second region, and the second spacer form a second space. The first space and the second space form the test solution retention space.

In another embodiment of the present invention, the first region and the second region face each other.

In the present embodiment, a spacer is disposed around the first region or around the second region, and the first region, the second region, and the spacer form the test solution retention space.

In a further embodiment of the present invention, a first spacer is disposed around the first region, and a first cover is disposed correspondingly to the first substrate with the first spacer interposed therebetween. The first region, the first spacer, and the first cover form a first space. A second spacer is disposed around the second region, and a second cover is disposed correspondingly to the second substrate with the second spacer interposed therebetween. The second region, the second spacer, and the second cover form a second space. The first space and the second space form the test solution retention space.

In yet another embodiment of the present invention, the cell comprises a first substrate having the first region on one face thereof and the second region on the other face thereof.

In the present embodiment, a first spacer is disposed around the first region, and a first cover is disposed correspondingly to the first substrate with the spacer interposed therebetween. A second spacer is disposed around the second region, and a second cover is disposed correspondingly to the first substrate with the second spacer interposed therebetween. The first region, the first spacer, and the first cover form a first space, and the second region, the second spacer, and the second cover form a second space. The first space and the second space form the test solution retention space.

ADVANTAGEOUS EFFECTS OF THE INVENTION

According to the present invention, a method in which concentrations of a plurality of biogenic substances can be easily detected with high accuracy, and an apparatus for biogenic substance concentration measurement of which size is easy to reduce, can be provided.

DESCRIPTION OF EMBODIMENTS

The present invention utilizes localized surface plasmon resonance of a metallic nanorod. Specifically, with respect to the resonant wavelength, the light intensity attenuation due to the effect of a first antigen and the light intensity attenuation due to the effect of a second antigen are respectively obtained. From the amount of shift in the wavelength which causes the light intensity attenuation to reach maximum, respective concentrations of the first antigen and the second antigen contained in a test solution can be easily measured with high accuracy.

(i) Step a

A cell comprising therein a first region, a second region, and a test solution retention space is used. The test solution containing the first antigen and the second antigen is supplied to the test solution retention space.

The first region and the second region may or may not face each other. The first region and the second region may or may not face the same direction in the cell. The first region and the second region are preferably disposed so that their respective main faces are parallel to each other.

On the first region, a plurality of first metallic nanorods with a first antibody on the surface thereof are immobilized. The first antibody specifically reacts with and bonds to the first antigen contained in the test solution. The first antibody can be selected as appropriate, depending on the kind of the first antigen.

On the second region, a plurality of second metallic nanorods with a second antibody on the surface thereof are immobilized. The second antibody specifically reacts with and bonds to the second antigen contained in the test solution. The second antibody can be selected as appropriate, depending on the kind of the second antigen.

The state in which a metallic nanorod is immobilized means, for example, a state in which the first metallic nanorod is deposited on the first region, that is, a state in which the first region and the first metallic nanorod are chemically or physically bonded to each other. The metallic nanorod is a metallic particulate or metal-coated dielectric particulate with a long axis and a short axis.

The first metallic nanorod and the second metallic nanorod (hereinafter also simply referred to as metallic nanorod) preferably have on their respective surfaces, at least one selected from the group consisting of gold, silver, copper, aluminum, and platinum. Particularly, it is more preferable that the metallic nanorod has on the surface thereof, gold, which has excellent chemical stability. The metallic nanorod with gold on the surface thereof exhibits at a wavelength near 520 nm and at a wavelength of 600 to 1500 nm, localized surface plasmon resonance bands originating from the short axis and the long axis, respectively. The first metallic nanorod and the second metallic nanorod may be of the same material or of a different material.

Figure 1:
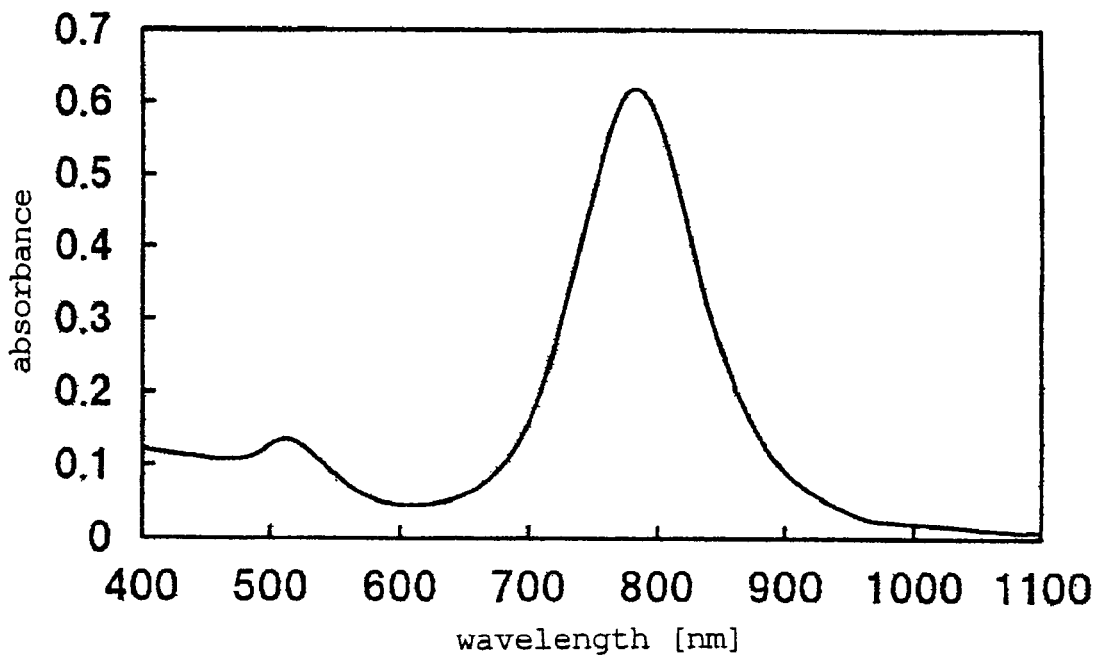
FIG. 1 illustrates an absorption spectrum of a metallic nanorod with gold on the surface thereof.

FIG. 1 shows an absorption spectrum of a metallic nanorod with gold on the surface thereof. The metallic nanorod according to FIG. 1 has a short axis with an average length of 10 nm and a long axis with an average length of 37 nm. At a wavelength near 510 nm and a wavelength near 780 nm, localized surface plasmon resonance bands originating from the short axis and the long axis are present, respectively.

The localized surface plasmon resonant wavelength originating from the long axis is preferably 700 to 1000 nm, in terms of not being easily absorbed by water and also by a number of biogenic substances.

The metallic nanorod preferably has a short axis of 2 nm or more and 100 nm or less, and a long axis of 20 nm or more and 500 nm or less. A ratio "X/Y" of a long axis "X" to a short axis "Y" is preferably 2 to 10.

In the cell according to the present invention, the respective long axes of the plurality of first metallic nanorods are aligned in the same direction. The respective long axes of the plurality of second metallic nanorods are also aligned in the same direction.

Figure 2A:
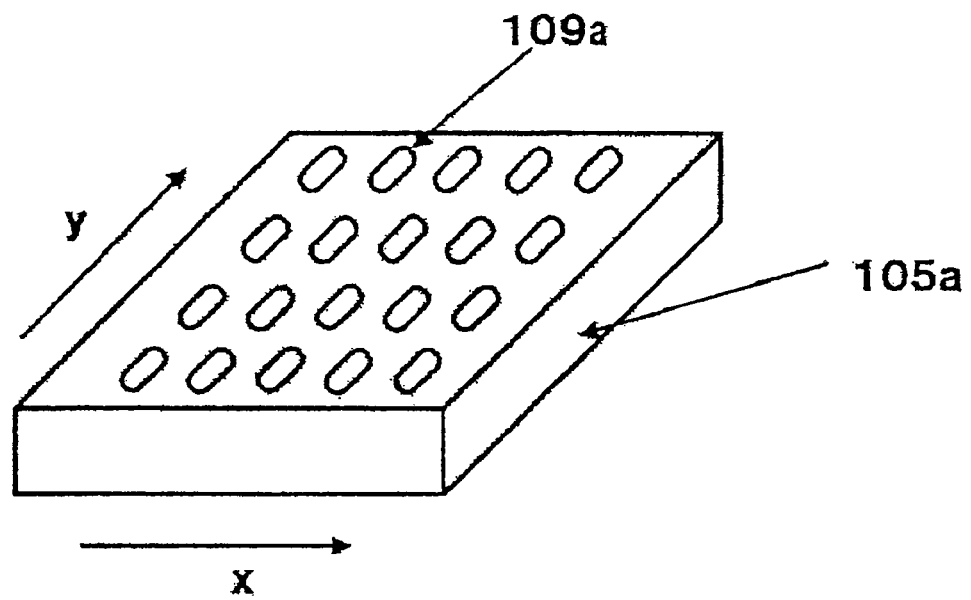
FIG. 2A schematically illustrates the constitution of a substrate on which a plurality of metallic nanorods are immobilized, with the respective long axes of the nanorods aligned in the same direction.
Figure 2B:
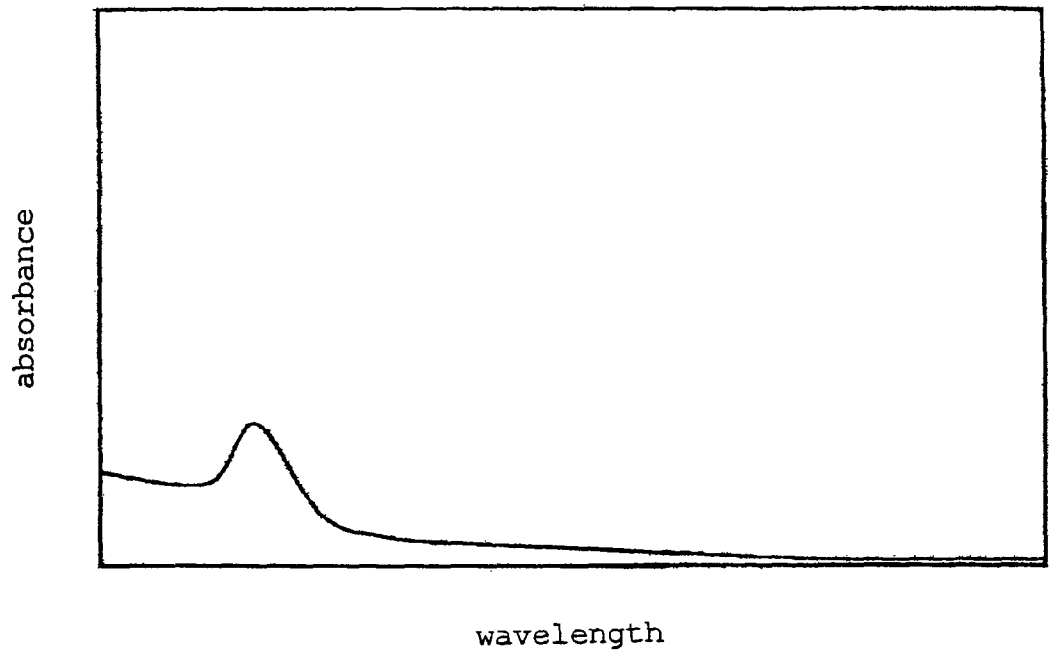
FIG. 2B shows an absorption spectrum of the metallic nanorods when radiating thereto a polarized light parallel to the short-axis direction thereof.
Figure 2C:
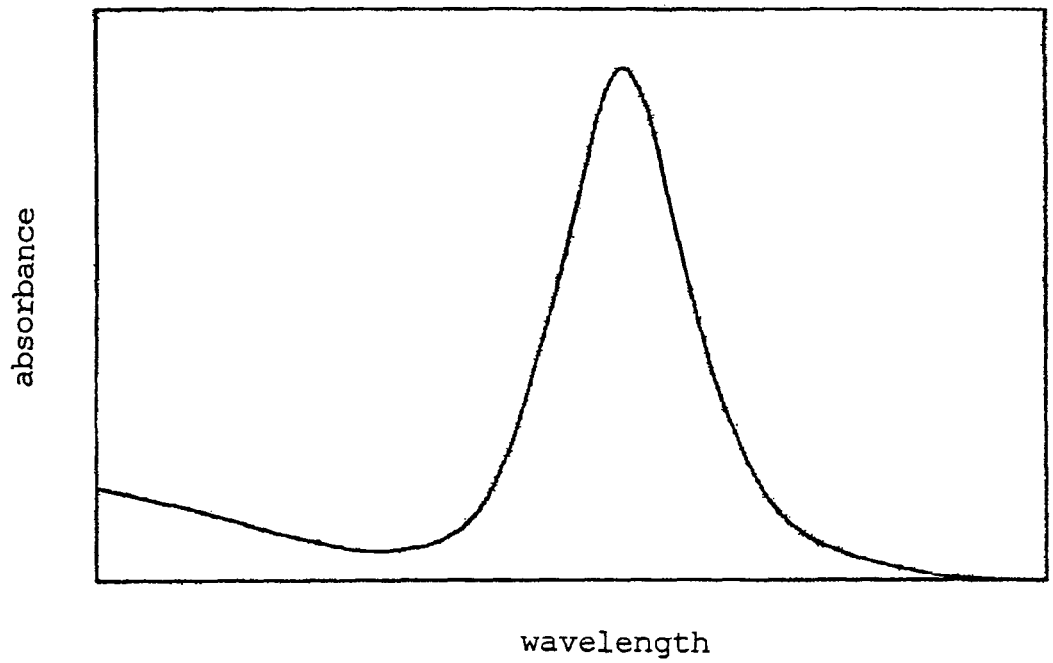
FIG. 2C shows an absorption spectrum of the metallic nanorods when radiating thereto a polarized light parallel to the long-axis direction thereof.

By aligning the respective long axes of the plurality of metallic nanorods in the same direction, a strong polarization property can be obtained. FIG. 2A schematically illustrates the constitution of a substrate on which a plurality of metallic nanorods 109a are immobilized, with the respective long axes of the nanorods aligned in the same direction. FIG. 2B shows an absorption spectrum of the metallic nanorods when radiating thereto a polarized light in a direction (direction "x" in FIG. 2A) perpendicular to the long-axis direction of the metallic nanorods, that is, a polarized light in a direction parallel to the short-axis direction. FIG. 2C shows an absorption spectrum of the metallic nanorods when radiating thereto a polarized light in a direction (direction "y" in FIG. 2A) parallel to the long-axis direction of the metallic nanorods. The respective metallic nanorods according to FIG. 2B and FIG. 2C have gold on their respective surfaces.

As shown in FIG. 2B and FIG. 2C, a substrate 105a exhibits only absorption by the localized surface plasmon resonance band originating from the short axis, for the polarized light in the direction "x". On the other hand, the substrate 105a exhibits only absorption by the localized surface plasmon resonance band originating from the long axis, for the polarized light in the direction "y".

In the metallic nanorod, the localized surface plasmon resonance band originating from the long axis is more perceptive to change in the refractive index of a nearby material, compared to the localized surface plasmon resonance band originating from the short axis. Therefore, the respective concentrations of the first antigen and the second antigen are calculated from the amount of shift in the resonant wavelength of the localized surface plasmon resonance band originating from the long axis. This enables the respective concentrations of the first antigen and the second antigen to be easily measured with high accuracy.

Figure 3A:
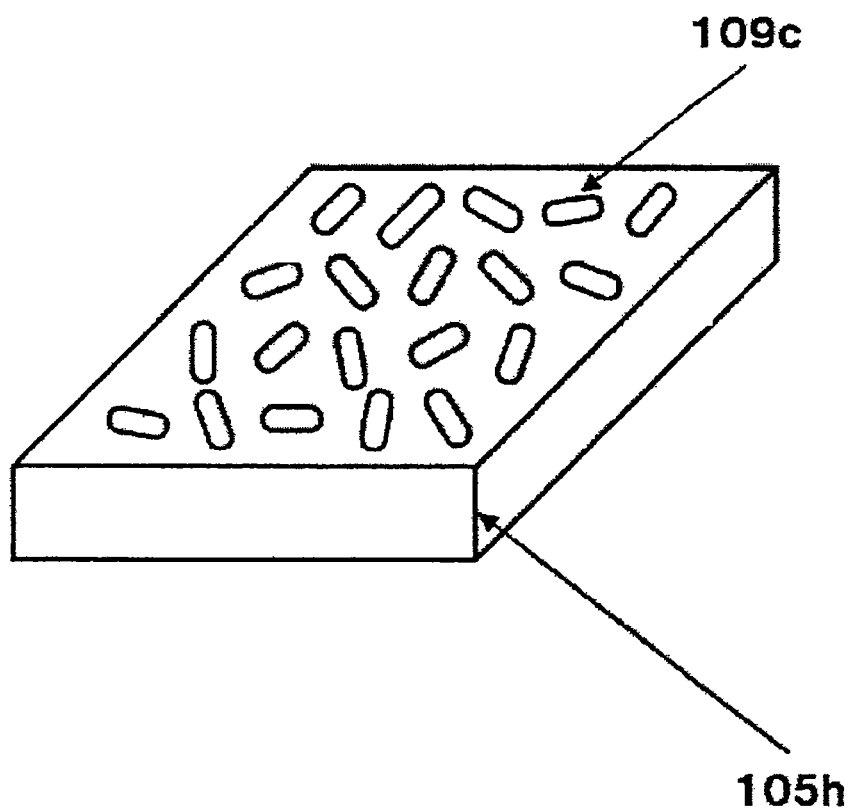
FIG. 3A schematically illustrates the constitution of a substrate on which a plurality of randomly-aligned metallic nanorods are immobilized.
Figure 3B:
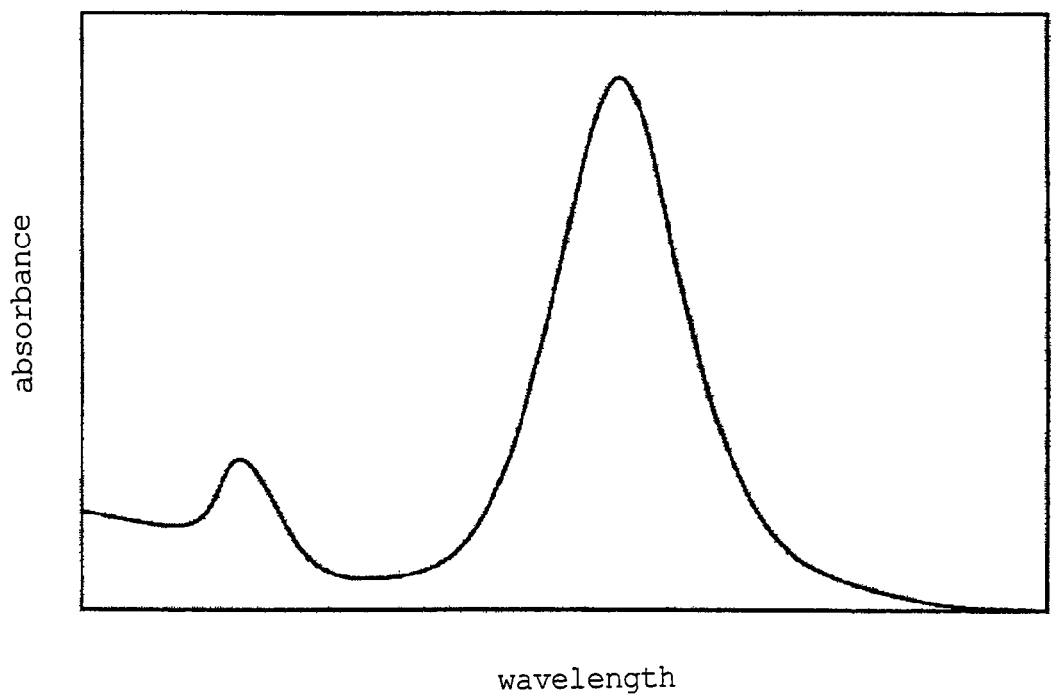
FIG. 3B shows an absorption spectrum of the metallic nanorods according to FIG. 3A.

On the other hand, there is no polarization property when the long-axis directions of the plurality of metallic nanorods are set, not in the same direction, but in random directions. FIG. 3A schematically illustrates the constitution of a substrate 105h on which a plurality of randomly-aligned metallic nanorods 109c are immobilized. FIG. 3B shows an absorption spectrum of the metallic nanorods according to FIG. 3A. The substrate 105h exhibits absorptions by the localized surface plasmon resonance bands originating from both the short axis and the long axis as shown in FIG. 3B, for a polarized light in any direction. Thus, it is difficult to measure the respective concentrations of the first antigen and the second antigen with high accuracy.

In the cell according to the present invention, the long-axis direction of the first metallic nanorod is orthogonal to the long-axis direction of the second metallic nanorod. In this state, a polarized light parallel to the long-axis direction of the plurality of first metallic nanorods is transmitted through the above-described cell, along an optical axis intersecting with the first region, the second region, and the test solution retention space. At this time, the light intensity attenuation reaches maximum at the wavelength of the localized surface plasmon resonance originating from the long axis of the first metallic nanorod. On the other hand, there is no light intensity attenuation at the wavelength of the localized surface plasmon resonance originating from the long axis of the second metallic nanorod. This enables observation of only the attenuation due to the effect of the first antigen, at the localized surface plasmon resonant wavelength.

When a polarized light parallel to the long-axis direction of the plurality of second metallic nanorods is transmitted through the above-described cell along the optical axis as described above, the light intensity attenuation does not occur at the wavelength of the localized surface plasmon resonance originating from the long axis of the first metallic nanorod 109a. On the other hand, at the wavelength of the localized surface plasmon resonance originating from the long axis of the second metallic nanorod 109b, the light intensity attenuation reaches maximum. This enables measurement of only the attenuation due to the effect of the second antigen, at the localized surface plasmon resonant wavelength.

Namely, the respective light intensity attenuations due to the respective effects of the first antigen and the second antigen can be measured with high accuracy, by a simple method of changing the direction of a polarized light transmitted through the cell according to the present invention. Therefore, the respective concentrations of the first antigen and the second antigen can be easily measured with high accuracy.

When the long-axis direction of the plurality of first metallic nanorods is not orthogonal to the long-axis direction of the plurality of second metallic nanorods, a polarized light parallel to the long-axis direction of the plurality of first metallic nanorods is affected by the long-axis direction of the plurality of second metallic nanorods. In this case, not only absorption by the localized surface plasmon resonance band originating from the long axis of the first metallic nanorod is caused, but absorption by the localized surface plasmon resonance band originating from the long axis of the second metallic nanorod is also caused. Therefore, an absorption spectrum specific to either one of the first metallic nanorod and the second metallic nanorod cannot be obtained. Thus, it is difficult to measure the respective concentrations of the first antigen and the second antigen with high accuracy.

(ii) Step b

In step b, the test solution containing the first antigen and the second antigen is supplied to the test solution retention space. This causes the first antigen and the second antigen to react with the first antibody on the first metallic nanorod surface and the second antibody on the second metallic nanorod surface, respectively.

Examples of the test solution include blood, perspiration, urine, saliva, tears, and the like.

For example, when the test solution is urine, the first antigen is albumin and the second antigen is creatinine. In this case, as the first antibody, an anti-albumin antibody can be given for example. As the second antibody, an anti-creatinine antibody can be given.

(iii) Step c

In step c, a polarized light parallel to the long-axis direction of the plurality of first metallic nanorods is transmitted through the cell, along an optical axis intersecting with the first region, the second region, and the test solution retention space. From a first light thus obtained, the concentration of the first antigen is calculated.

By transmitting a polarized light parallel to the long-axis direction of the plurality of first metallic nanorods through the cell, absorption by the localized surface plasmon resonance band originating from the long axis of the first metallic nanorod, namely, such affected by the first antigen, is caused. The wavelength at which attenuation of the intensity of the first light reaches maximum, is a localized surface plasmon resonant wavelength (first wavelength). Since the polarized light parallel to the long-axis direction of the first metallic nanorod is orthogonal to the long-axis direction of the second metallic nanorod, the light intensity attenuation originating from the long axis of the second metallic nanorod does not occur.

Herein, the localized surface plasmon resonant wavelength of the first metallic nanorod not affected by the first antigen is obtained in advance.

The first wavelength is compared with the localized surface plasmon resonant wavelength not affected by the first antigen. From the amount of shift in the wavelength, the concentration of the first antigen can be calculated.

(iv) Step d

In step d, a polarized light parallel to the long-axis direction of the plurality of second metallic nanorods is transmitted through the cell, along the optical axis as in step c. From a second light thus obtained, the concentration of the second antigen is calculated.

By transmitting a polarized light parallel to the long-axis direction of the plurality of second metallic nanorods through the cell, absorption by the localized surface plasmon resonance band originating from the long axis of the second metallic nanorod, namely, such affected by the second antigen, is caused. The wavelength at which attenuation of the intensity of the second light reaches maximum, is a localized surface plasmon resonant wavelength (second wavelength). Since the polarized light parallel to the long-axis direction of the second metallic nanorod is orthogonal to the long-axis direction of the first metallic nanorod, the light intensity attenuation originating from the long axis of the first metallic nanorod does not occur.

As in step c, the localized surface plasmon resonant wavelength of the second metallic nanorod not affected by the second antigen is obtained in advance. The second wavelength is compared with the localized surface plasmon resonant wavelength not affected by the second antigen. From the amount of shift in the wavelength, the concentration of the second antigen can be calculated.

There is no particular limitation to the method for transmitting a polarized light parallel to the long-axis direction of the plurality of second metallic nanorods through the cell, along the optical axis as in step c. In the present invention, for example, an apparatus for biogenic substance concentration measurement is used, the apparatus comprising: a cell having a first region, a second region, and a test solution retention space; a light source for radiating polarized light to the cell, or a polarizing plate; and a photoreceiver for receiving light transmitted through the cell.

In this case, at least one of: the light source for radiating polarized light to the cell; the polarizing plate; and the cell may be rotated with the optical axis as the axis. By immobilizing the light source, the polarizing plate, or the cell at a position where the polarized light parallel to the long-axis direction of the plurality of second metallic nanorods can be radiated to the cell, the desired polarized light can be transmitted through the cell.

Thus, a polarized light to be transmitted through the cell can switch directions, between that parallel to the long-axis direction of the plurality of first metallic nanorods and that parallel to the long-axis direction of the plurality of second metallic nanorods. Thus, the above-described step c and step d can be carried out easily. This enables the respective absorption spectra affected by the first antigen and the second antigen to be obtained easily.

Namely, according to the present invention, it is unnecessary to control the positional relation among the light source, the first region, the second region, and the photoreceiver, and to move the cell. Therefore, deviation of the optical axis is suppressed. Further, it is also unnecessary to provide a plurality of optical axes for radiating light, and to widen the range for radiating light.

In the following, embodiments of the present invention will be explained with reference to drawings.

Embodiment 1

The present embodiment will be explained using FIGS. 4 to 6.

Figure 4:
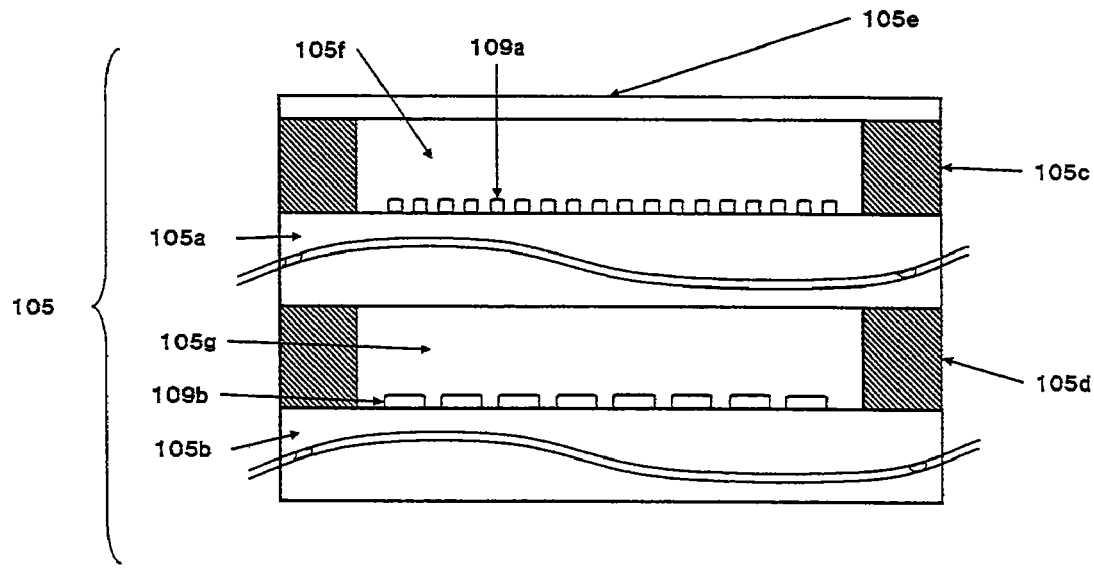
FIG. 4 schematically illustrates the cross section of a cell according to Embodiment 1 of the present invention.

FIG. 4 schematically illustrates a cross section of a cell according to the present embodiment.

The cell 105 comprises a first substrate 105a, a second substrate 105b, a first spacer 105c, a second spacer 105d, and a cover glass 105e.

The first substrate 105a has a first region on one face thereof. On the first region, a plurality of first metallic nanorods 109a are immobilized. The respective long axes of the plurality of first metallic nanorods 109a are aligned in the same direction. As one example of the average size of the first metallic nanorod, the respective average lengths of the long axis and the short axis are 37 nm and 10 nm, respectively.

The first region may be the entire face of the first substrate or a part of the face thereof. The first substrate preferably has an area of 100 $\mu m^2$ or larger.

The second substrate 105b has a second region on one face thereof. On the second region, a plurality of second metallic nanorods 109b are immobilized. The respective long axes of the plurality of second metallic nanorods 109b are aligned in the same direction. As one example of the average size of the second metallic nanorod, the respective average lengths of the long axis and the short axis are 37 nm and 10 nm, respectively, as with the first metallic nanorod.

The second region may be the entire face of the second substrate or a part of the face thereof. The second substrate preferably has an area of 100 $\mu m^2$ or larger.

Known technologies can be applied without any particular limitation as a method for immobilizing on the substrate, the plurality of metallic nanorods of which the respective long axes are aligned in the same direction. For example, a mask having a predetermined pattern is formed on the substrate by using x-ray lithography or electron-beam lithography. Metal is sputtered on this substrate, and by removing the mask thereafter, a substrate on which metallic nanorods are formed in a desired pattern can be obtained.

Alternatively, a metal mold is created on an Si substrate by using x-ray lithography or electron beam lithography. By pressing the metal mold onto a resin, a pattern is transferred onto the resin. Namely, resin nanorods are produced by using nanoprint technology. Subsequently, metal nanorods having metal on their respective surfaces are obtained by sputtering metal.

Other than the above, metallic nanorods may be synthesized by known technologies such as a synthesis method using chemical reactions and a synthesis method using photoreactions.

For example, a paste containing metallic nanorods, a dispersant, a solvent, and a resin is applied to a substrate. At this time, for example, the paste is applied by applying a certain amount of shear stress in a direction opposite to that of the substrate movement, by means of a micro-gravure coater. Alternatively, an electric or magnetic force may be applied in a fixed direction, during or after paste application. By these methods, the respective long axes of the plurality of metallic nanorods can be aligned in the same direction.

As illustrated in FIG. 4, the first spacer 105c is disposed around the first region. The cover glass 105e is disposed correspondingly to the first substrate 105a with the first spacer 105c interposed therebetween. The first region, the first spacer 105c, and the cover glass 105e form a first space 105f.

The second spacer 105d is disposed around the second region. The other face of the first substrate 105a, the second region, and the second spacer 105d form a second space 105g.

The first space 105f and the second space 105g each independently comprise a supply inlet and a discharge outlet (not illustrated) for a test solution. The first space 105f and the second space 105g correspond to a test solution retention space. The first region, the second region, the first space, and the second space are disposed so as to intersect with one optical axis.

Figure 5:
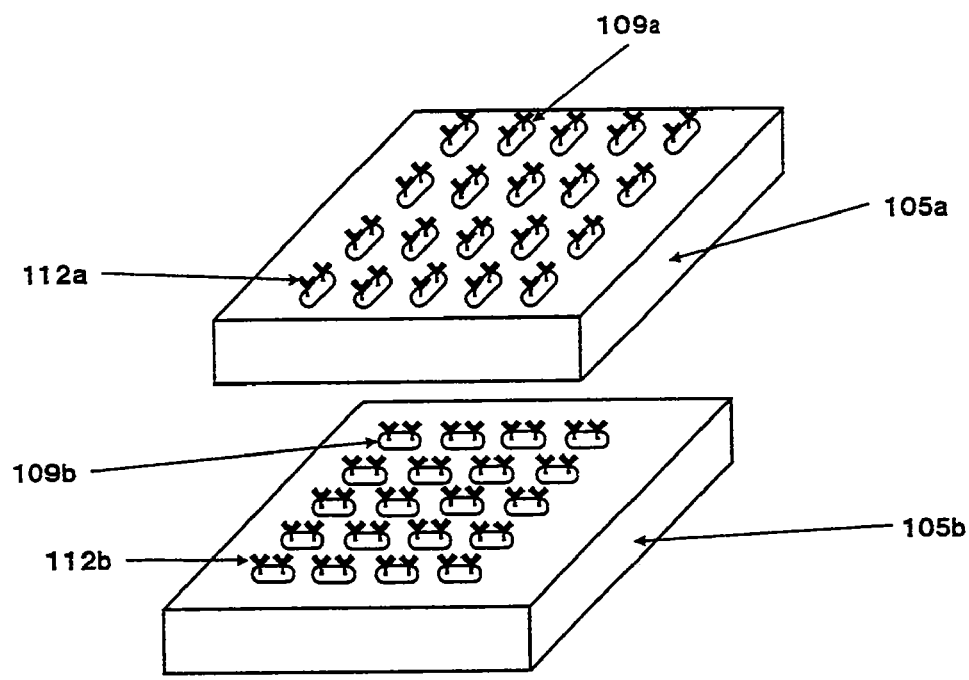
FIG. 5 schematically illustrates a first substrate and a second substrate according to Embodiment 1 of the present invention.

FIG. 5 schematically illustrates the first substrate 105a and the second substrate 105b according to the present embodiment. The long-axis direction of the first metallic nanorod 109a is orthogonal to the long-axis direction of the second metallic nanorod 109b. The first substrate 105a and the second substrate 105b are disposed so that their respective main faces are parallel. The first region and the second region face the same direction.

The surface of the first metallic nanorod 109a has a first antibody 112a. The first antibody 112a reacts with and bonds to a first antigen contained in the test solution. The surface of the second metallic nanorod 109b has a second antibody 112b. The second antibody 112b reacts with and bonds to a second antigen contained in the test solution.

The respective materials of the first substrate 105a, the second substrate 105b, and the cover glass 105e may be known materials that transmit light of wavelengths of a halogen light source 101. For example, $SiO_2$ is preferable as being transparent to the wavelengths of the above-mentioned light. Specific examples include quartz glass, single crystal of $SiO_2$, and the like.

An apparatus for biogenic substance concentration measurement comprises a cell and an optical measuring apparatus. The optical measuring apparatus comprises a light source, a polarizing plate, and a photoreceiver. The optical measuring apparatus may further comprise a spectroscopic apparatus for separating light transmitted through the cell, a rotating apparatus for rotating the cell or the polarizing plate, a calculating unit, and a memory unit.

Figure 6:
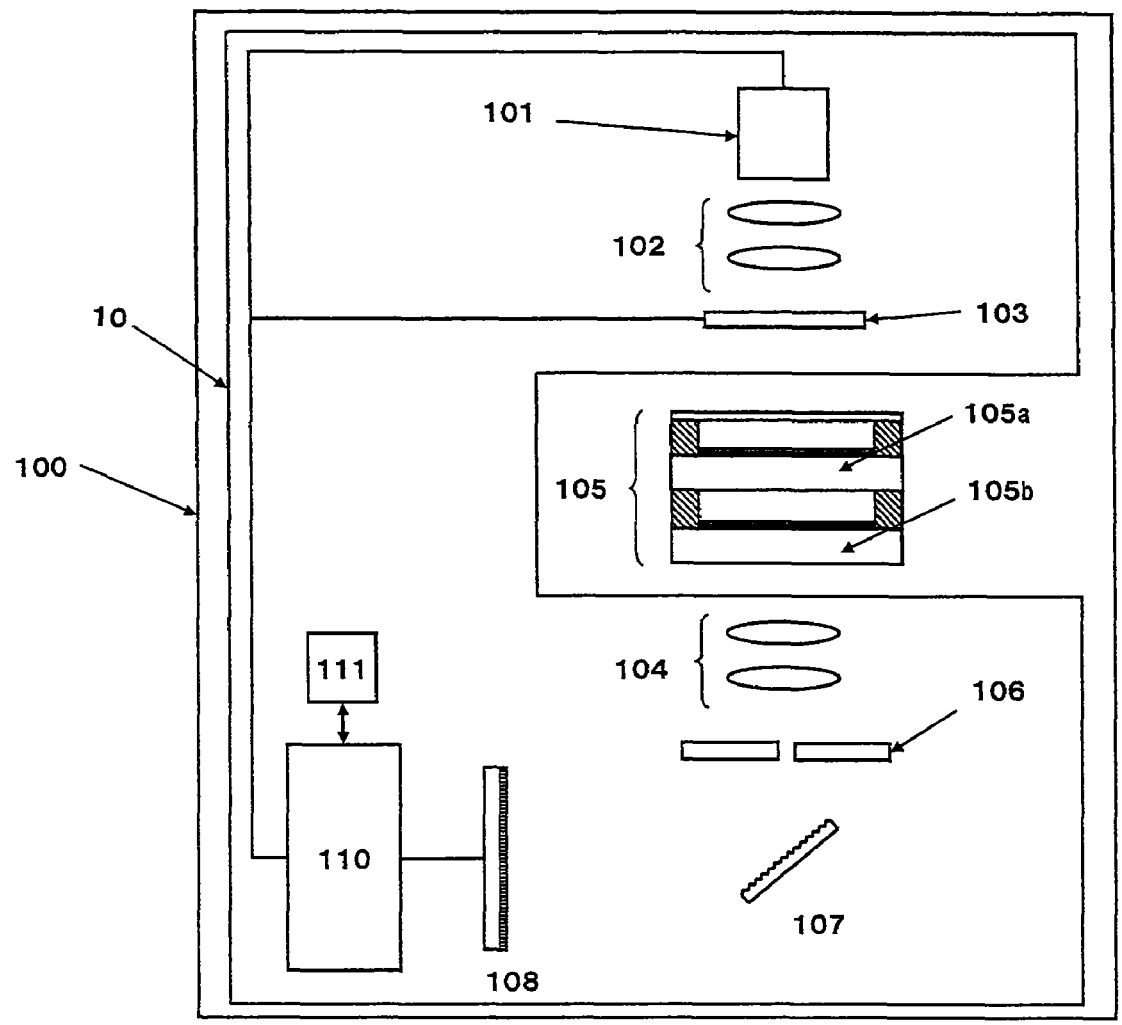
FIG. 6 schematically illustrates the constitution of an apparatus for biogenic substance concentration measurement according to Embodiment 1 of the present invention.

FIG. 6 schematically illustrates the constitution of an apparatus for biogenic substance concentration measurement according to Embodiment 1 of the present invention. The biogenic substance concentration measuring apparatus 100 in FIG. 6 comprises the cell 105 described above and an optical measuring apparatus 10.

The optical measuring apparatus 10 comprises the halogen light source 101 as the light source, lenses 102, a polarizing plate 103, lenses 104, slits 106, a grating device 107, a photoreceiver 108, a microcomputer 110 as the calculating unit, and a memory 111 as the memory unit. The slits 106 and the grating device 107 constitute the spectroscopic apparatus. The cell 105 is disposed between the polarizing plate 103 and the lenses 104. In the optical measuring apparatus 10, the polarizing plate 103 is capable of rotating with the optical axis intersecting with the first region, the second region, and the test solution retention space as the rotation axis.

The halogen light source 101 radiates light including a localized surface plasmon resonant wavelength. The lenses 102 adjust the light which the halogen light source 101 radiates thereto.

The light source may be such that radiates light including the localized surface plasmon resonant wavelength of the metallic nanorod.

In the present embodiment, the light source is the halogen light source 101 of which light is unpolarized. However, for example, a light source which radiates polarized light may also be used. In such a case, a wave plate for rotating the polarized light may be used in place of the polarizing plate. As the light source which radiates polarized light, a laser light source or the like can be given.

The polarizing plate 103 selects the polarization of the light to be adjusted by the lenses 102. The polarizing plate is not particularly limited, and for example, a known polarizing plate such as a polarizing film using organic molecules can be used.

For the rotating apparatus, for example, a motor (not illustrated) is used. When the light source which radiates polarized light is used, the direction of the polarized light may be controlled by rotating the light source with the rotating apparatus.

The lenses 104 adjust the light transmitted through the cell 105.

The slits 106 and the grating device 107 constituting the spectroscopic apparatus separate the light transmitted through the cell into predetermined wavelengths. The slits 106 adjust the light transmitted through the lenses 104 to substantially be in a form of a point light. The grating device 107 reflects while also separating according to the wavelengths, the light transmitted through the slits 106.

The spectroscopic apparatus is not particularly limited, and a known spectroscopic apparatus capable of separating light into predetermined wavelengths can be used. As other spectroscopic apparatuses, for example, a spectral filter such as an interference filter, and an acousto-optic device can be used.

The photoreceiver 108 detects light separated by the spectroscopic apparatus. The photoreceiver is not particularly limited, and for example, a known technology can be used. For example, CCD (Charge Coupled Device), CMOS, and a one-dimensional photodetector array, each having a plurality of photo-receptive regions, can be used. For example, a one-dimensional CCD element having 4096 photo-receptive regions can be used. Alternatively, a photoreceiver having a single photo-receptive region can also be used.

The microcomputer 110 as the calculating unit calculates the resonant wavelength of a localized surface plasmon resonance, and calculates the biogenic substance concentration from the amount of shift in the resonant wavelength. The microcomputer 110 calculates the localized surface plasmon resonant wavelength from the intensity of light detected by the photoreceiver 108. Further, the microcomputer 110 calculates the respective concentrations of the first antigen and the second antigen contained in the test solution, based on the localized surface plasmon resonant wavelength.

The memory 111 as the memory unit stores information on the state of the polarized light, information on the angle of rotation of the cell, information related to wavelengths, and the like. The information on the state of the polarized light includes that on the direction of the polarized light transmitted through the cell. The information related to wavelengths includes those on, for example: the wavelengths corresponding to the respective photo-receptive regions of the photoreceiver 108; the correlation between the amount of shift in the localized surface plasmon resonant wavelength, and the concentration of the first antigen or that of the second antigen; the wavelength of the localized surface plasmon resonance of the first metallic nanorod not affected by the first antigen; and the wavelength of the localized surface plasmon resonance of the second metallic nanorod not affected by the second antigen.

The correlation between the localized surface plasmon resonant wavelength and the concentration of the first antigen contained in the test solution or that of the second antigen contained therein can be obtained by, for example, the following method.

First, the localized surface plasmon resonant wavelength of a test solution having a known biogenic substance concentration is measured. This measurement is conducted on a number of test solutions, each having a different biogenic substance concentration. Thus, data on biogenic substance concentrations corresponding to the respective wavelengths can be obtained.

The cell 105 preferably comprises a sensor (not illustrated) for determining whether or not the test solution is sufficiently supplied to the test solution retention space. For example, the cover glass 105e and the first substrate 105a comprise a first electrode pair. The first substrate 105a and the second substrate 105b comprise a second electrode pair. Thus, when the cell 105 is inserted into the optical measuring device 10, a weak voltage is applied to the electrodes. Herein, test solutions such as blood contain an electrolyte. Therefore, a current flows between the electrodes when the test solution is supplied to the cell. Thus, it is possible to determine whether or not the test solution is sufficiently supplied to the test solution retention space. The power of the halogen light source 101 may be turned on automatically by utilizing the output of the sensor. Thus, biogenic substance concentration measurement can be automated.

Next, operation of the apparatus for biogenic substance concentration measurement according to the present embodiment will be explained with reference to drawings.

First, the test solution containing the first antigen and the second antigen is supplied to the cell 105.

Thus, the first antigen reacts specifically with and bonds to the first antibody 112a on the surface of the first metallic nanorod 109a. The second antigen reacts specifically with and bonds to the second antibody 112b on the surface of the second metallic nanorod 109b.

After allowing the first antibody 112a and the second antibody 112b to react sufficiently with the first antigen and the second antigen, respectively, the cell 105 is inserted into the optical measuring apparatus 10.

Subsequently, the power of the halogen light source 101 is turned on. The light emitted from the halogen light source 101 is adjusted by the lenses 102, and passes through the polarizing plate 103. Next, the polarized light transmitted through the polarizing plate 103 is set parallel to the long-axis direction of the plurality of first metallic nanorods 109a. At this time, the polarizing plate 103 or the light source which radiates polarized light is rotated, if necessary.

(Measurement of First Wavelength)

The polarized light is transmitted through the cell 105 along a predetermined optical axis. The optical axis is set so as to intersect with the first region of the first substrate 105a, the second region of the second substrate 105b, the first space 105f, and the second space 105g.

The light transmitted through the cell 105 (first light) is collected by the lenses 104. The first light is transmitted through the slits 106, separated by the grating device 107, and then detected by the photoreceiver 108.

At this time, attenuation of the intensity of the first light reaches maximum at the wavelength of the localized surface plasmon resonance originating from the long axis of the first metallic nanorod 109a. On the other hand, attenuation of the intensity of the first light does not occur at the wavelength of the localized surface plasmon resonance originating from the long axis of the second metallic nanorod 109b.

The microcomputer 110 determines the wavelength (first wavelength) at which attenuation of the intensity of the first light reaches maximum. The first wavelength is stored in the memory 111. The first wavelength is the wavelength of the localized surface plasmon resonance originating from the long axis of the first metallic nanorod 109a, namely, such affected by the first antigen.

(Measurement of Second Wavelength)

The microcomputer 110 rotates the polarizing plate 103 by 90°. This allows the polarized light to be set parallel to the long-axis direction of the plurality of second metallic nanorods 109b.

The polarized light is transmitted through the cell 105 along the optical axis as that for measuring the first wavelength.

The light (second light) transmitted through the cell is separated and then detected by the photoreceiver 108, as with the first light.

As this time, attenuation of the intensity of the second light does not occur at the wavelength of the localized surface plasmon resonance originating from the long axis of the first metallic nanorod 109a. On the other hand, attenuation of the intensity of the second light reaches maximum at the wavelength of the localized surface plasmon resonance originating from the long axis of the second metallic nanorod 109b.

The microcomputer 110 determines the wavelength (second wavelength) at which attenuation of the intensity of the second light reaches maximum. The second wavelength is stored in the memory 111. The second wavelength is the wavelength of the localized surface plasmon resonance originating from the long axis of the second metallic nanorod 109a, namely, such affected by the second antigen.

(Concentration of First Antigen)

The microcomputer 110 reads out from the memory 111, a wavelength (first reference wavelength) of the localized surface plasmon resonance originating from the long axis of the first metallic nanorod prior to the first antigen bonding to the first antibody 112a. The first reference wavelength is not affected by the first antigen. The microcomputer 110 compares the first wavelength with the first reference wavelength and obtains the wavelength shift amount.

Subsequently, the microcomputer 110 calculates the concentration of the first antigen, by referring to the correlation between the wavelength shift amount of the first wavelength and the concentration of the first antigen in the memory 111.

(Concentration of Second Antigen)

The microcomputer 110 reads out from the memory 111, a wavelength (second reference wavelength) of the localized surface plasmon resonance originating from the long axis of the second metallic nanorod prior to the second antigen bonding to the second antibody 112b. The second reference wavelength is not affected by the second antigen. The microcomputer 110 compares the second wavelength with the second reference wavelength and obtains the wavelength shift amount.

Subsequently, the microcomputer 110 calculates the concentration of the second antigen, by referring to the correlation between the wavelength shift amount of the second wavelength and the concentration of the second antigen in the memory 111.

The respective concentrations of the first antigen and the second antigen thus obtained are notified to the user by sound through a speaker (not illustrated), indication on a display (not illustrated), or the like.

Embodiment 2

Another embodiment of the present invention will be explained using FIGS. 7 to 9.

Figure 7:
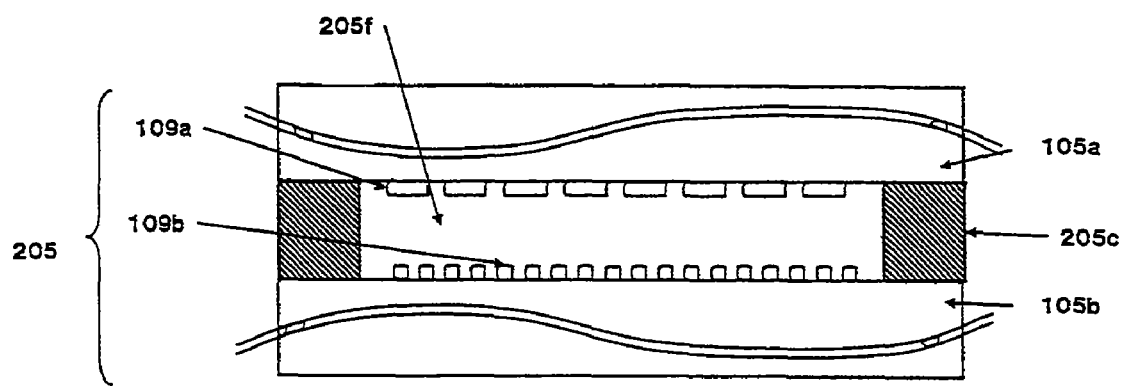
FIG. 7 schematically illustrates the cross section of a cell according to Embodiment 2 of the present invention.
Figure 8:
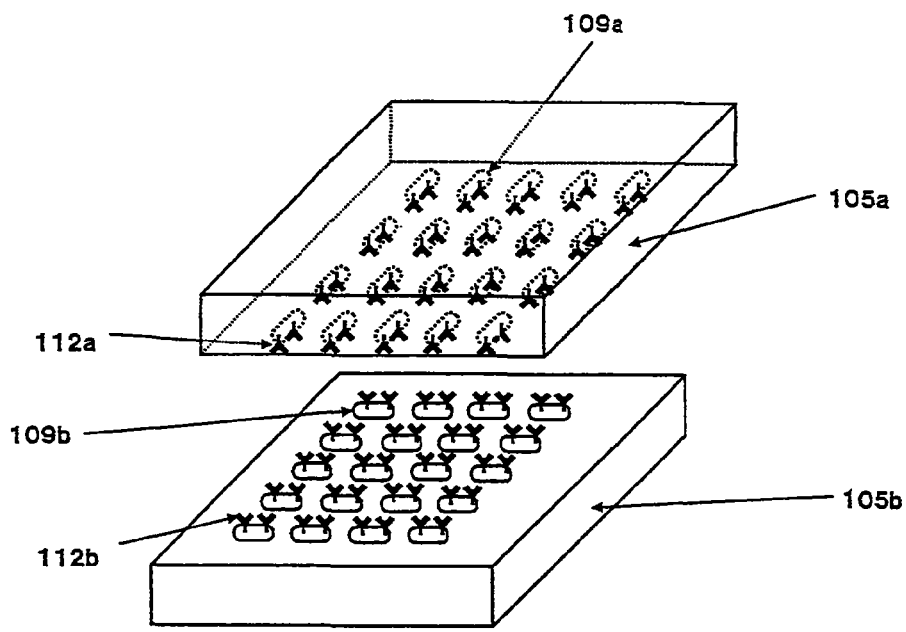
FIG. 8 schematically illustrates a first substrate and a second substrate according to Embodiment 2 of the present invention.
Figure 9:
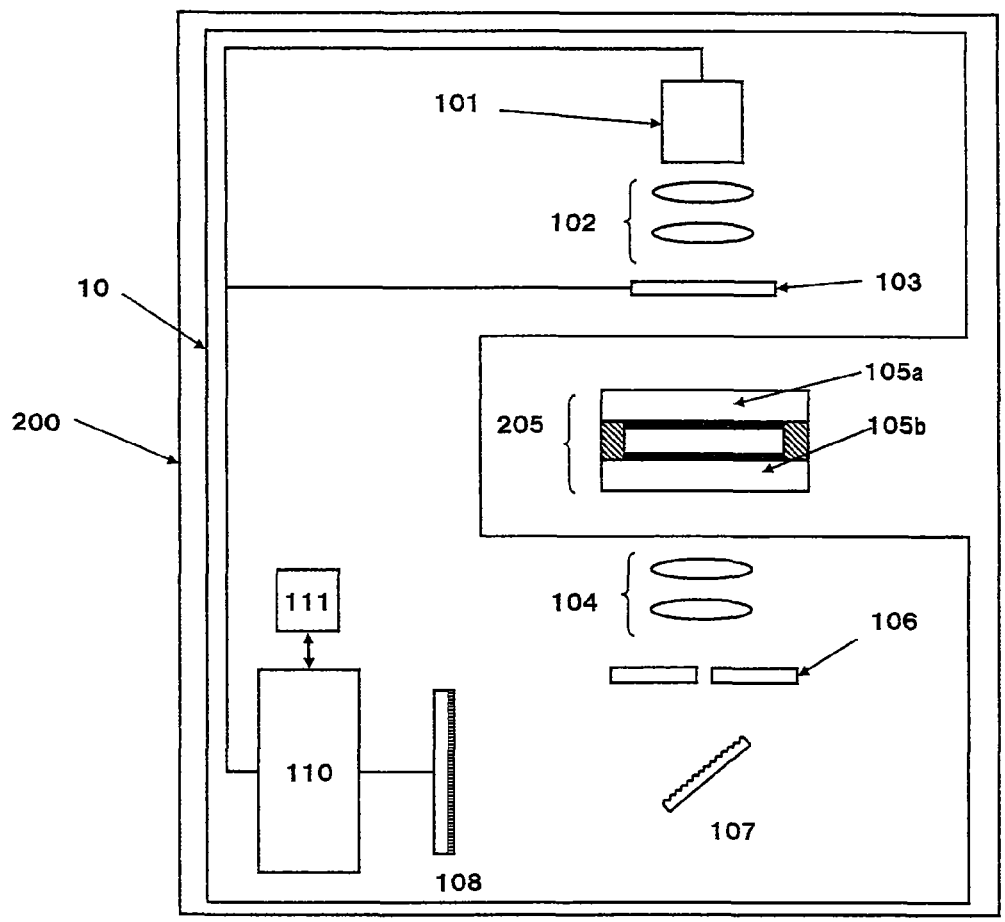
FIG. 9 schematically illustrates the constitution of an apparatus for biogenic substance concentration measurement according to Embodiment 2 of the present invention.

In FIGS. 7 to 9, for the same components as in FIGS. 4 to 6, the same corresponding reference numerals will be used and explanation will be omitted.

FIG. 7 schematically illustrates the cross section of a cell according to the present embodiment.

The cell 205 comprises the first substrate 105a and the second substrate 105b as in Embodiment 1, and a spacer 205c. The spacer 205c is disposed around the first region or around the second region. The first region, the second region, and the spacer 205c form a test solution retention space 205f. The first region, the second region, and the test solution retention space are disposed so as to intersect with one optical axis. The test solution retention space 205f comprises a supply inlet and a discharge outlet (not illustrated).

FIG. 8 schematically illustrates the first substrate 105a and the second substrate 105b according to the present embodiment. The long-axis direction of the first metallic nanorod 109a is orthogonal to the long-axis direction of the second metallic nanorod 109b. The first substrate 105a and the second substrate 105b are disposed so that their respective main faces are parallel. The first region and the second region face each other. The surface of the first metallic nanorod 109a has the first antibody 112a. The surface of the second metallic nanorod 109b has the second antibody 112b.

When the test solution containing the first antigen and the second antigen is supplied to the test solution retention space 205f, the first antigen reacts specifically with and bonds to the first antibody 112a on the surface of the first metallic nanorod 109a. The second antigen reacts specifically with and bonds to the second antibody 112b on the surface of the second metallic nanorod 109b.

FIG. 9 schematically illustrates the constitution of an apparatus for biogenic substance concentration measurement according to the present embodiment. The biogenic substance concentration measuring apparatus 200 in FIG. 9 has the same constitution as in Embodiment 1, except for comprising the above-described cell 205.

In the present embodiment, since the number of the test solution retention space is one, the constitution of the sensor for determining whether or not the test solution is filled also becomes simple.

Operation of the apparatus for biogenic substance concentration measurement according to the present embodiment is basically the same as that in Embodiment 1. Therefore, explanation will be omitted. Since the number of the test solution retention space is one in the cell according to the present embodiment, the test solution can be easily supplied. Further, it is also easy to produce the cell.

Embodiment 3

Figure 10:
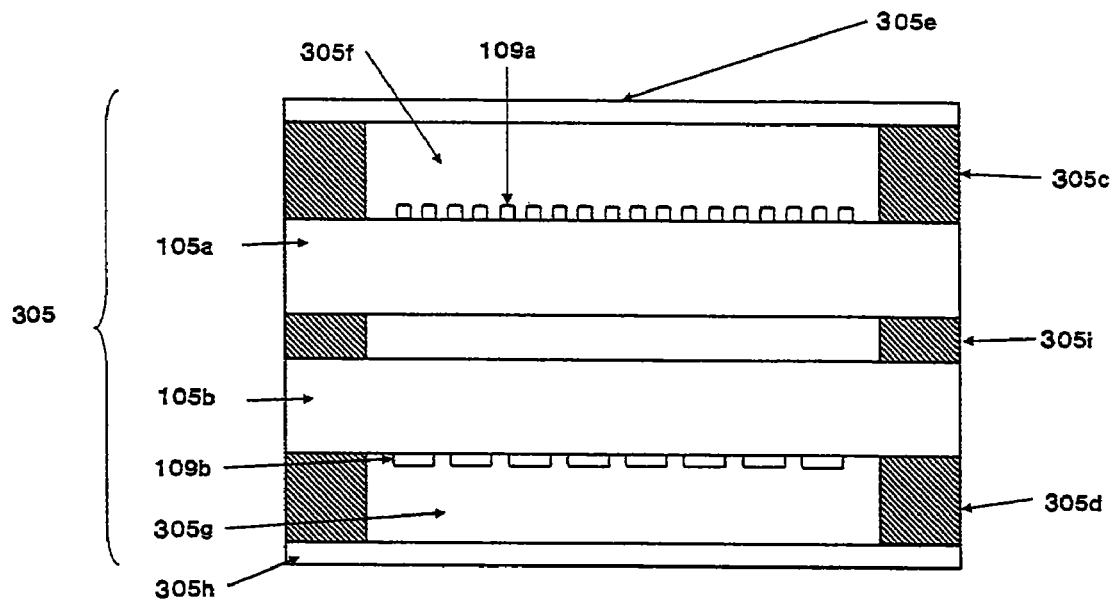
FIG. 10 schematically illustrates the cross section of a cell according to Embodiment 3 of the present invention.
Figure 11:
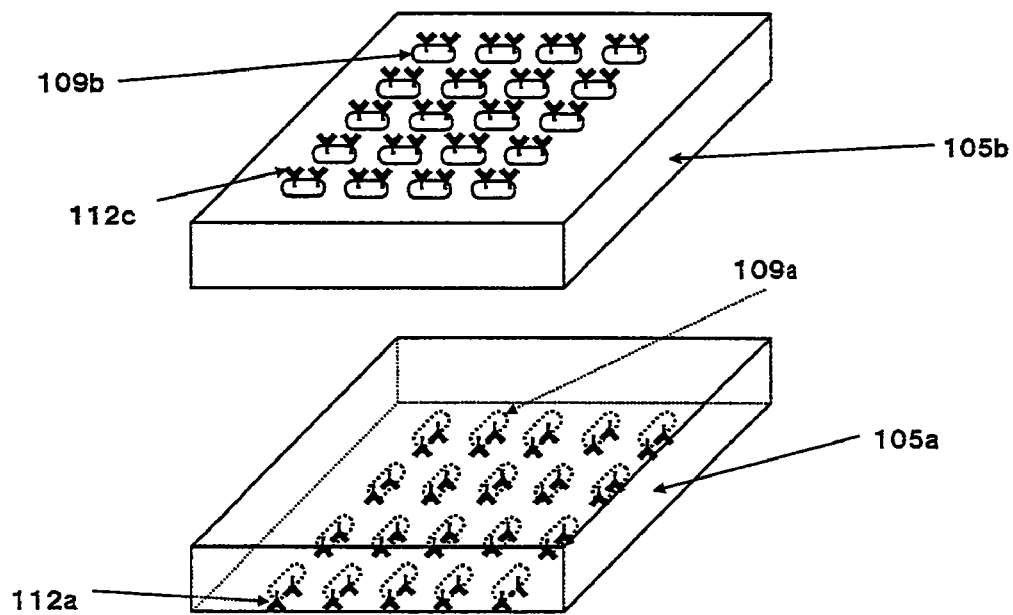
FIG. 11 schematically illustrates a first substrate and a second substrate according to Embodiment 3 of the present invention.
Figure 12:
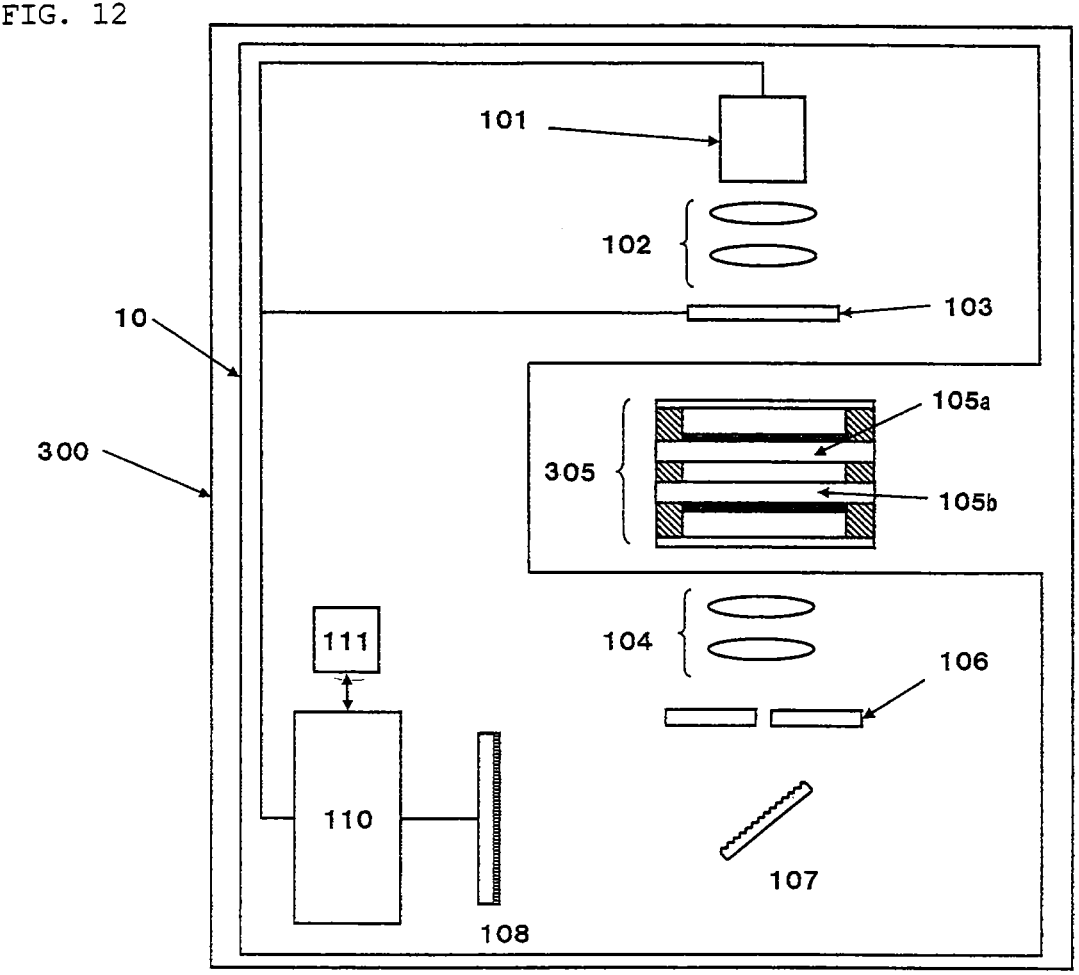
FIG. 12 schematically illustrates the constitution of an apparatus for biogenic substance concentration measurement according to Embodiment 3 of the present invention.

A further embodiment of the present invention will be explained using FIGS. 10 to 12. In FIGS. 10 to 12, for the same components as in FIGS. 4 to 6, the same corresponding reference numerals will be used and explanation will be omitted.

FIG. 10 schematically illustrates the cross section of a cell according to the present embodiment.

The cell 305 comprises the first substrate 105a and the second substrate 105b as in Embodiment 1, a first cover glass 305e, a second cover glass 305h, a first spacer 305c, a second spacer 305d, and a third spacer 305i.

The first spacer 305c is disposed around the first region. The first cover glass 305e is disposed correspondingly to the first substrate 105a with the first spacer 305c interposed therebetween. The first region, the first spacer 305c, and the first cover glass 305e form a first space 305f.

The second spacer 305d is disposed around the second region. The second cover glass 305h is disposed correspondingly to the second substrate 105b with the second spacer 305d interposed therebetween. The second region, the second spacer 305d, and the second cover glass 305h form a second space 305g. The third spacer 305i is disposed between the first substrate 105a and the second substrate 105b.

The first space 305f and the second space 305g are each independently comprise a supply inlet and a discharge outlet (not illustrated) for the test solution. The first space 305f and the second space 305g form the test solution retention space. The first region, the second region, the first space, and the second space are disposed so as to intersect with one optical axis.

FIG. 11 schematically illustrates the first substrate 105a and the second substrate 105b according to the present embodiment. In FIG. 11, the long-axis direction of the first metallic nanorod 109a is orthogonal to the long-axis direction of the second metallic nanorod 109b. The first substrate 105a and the second substrate 105b are disposed so that their respective main faces are parallel. The first region and the second region do not face the same direction, nor do they face each other. The surface of the first metallic nanorod 109a has the first antibody 112a. The surface of the second metallic nanorod 109b has the second antibody 112b.

FIG. 12 schematically illustrates the constitution of an apparatus for biogenic substance concentration measurement according to the present embodiment. The biogenic substance concentration measuring apparatus 300 has the same constitution as in Embodiment 1, except for comprising the above-described cell 305.

Since operation of the apparatus for biogenic substance concentration measurement according to the present embodiment is basically the same as in Embodiment 1, explanation will be omitted. In the cell according to the present embodiment, the first space and the second space are independent of each other, and therefore, one is not affected by the antibody of the other. Thus, the respective concentrations of the first antigen and the second antigen can be measured with high accuracy. Further the cell can be easily produced, by producing identical substrates for the first substrate and the second substrate and bonding them together so that their respective metallic nanorods are orthogonal to each other.

Embodiment 4

Yet another embodiment of the present invention will be explained using FIGS. 13 to 15.

Figure 13:
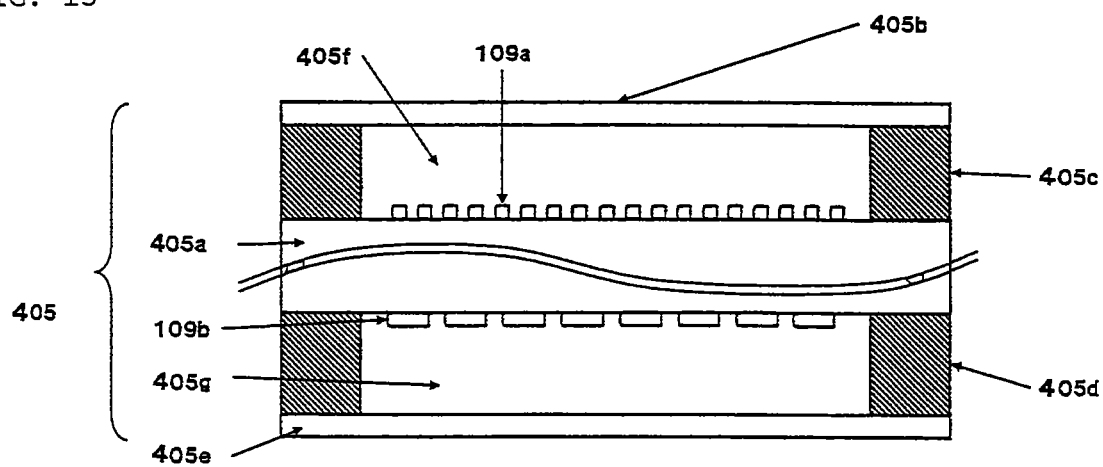
FIG. 13 schematically illustrates the cross section of a cell according to Embodiment 4 of the present invention.

FIG. 13 schematically illustrates the cross section of a cell according to the present embodiment.

The cell 405 comprises a substrate 405a, a first cover glass 405b, a second cover glass 405e, a first spacer 405c, and a second spacer 405d. The substrate 405a has a first region on one face thereof on which the plurality of first metallic nanorods 109a are immobilized, and a second region on the other face thereof on which the plurality of second metallic nanorods 109b are immobilized.

The first spacer 405c is disposed around the first region. The first cover glass 405b is disposed correspondingly to the substrate 405a with the first spacer 405c interposed therebetween. The first region, the first spacer 405c, and the first cover glass 405b form a first space 405f.

The second spacer 405d is disposed around the second region. The second cover glass 405e is disposed correspondingly to the substrate 405a with the second spacer 405d interposed therebetween. The second region, the second spacer 405d, and the second cover glass 405e form a second space 405g.

The first space 405f and the second space 405g are each independently comprise a supply inlet and a discharge outlet (not illustrated) for the test solution. The first space 405f and the second space 405g form the test solution retention space. The first region, the second region, the first space, and the second space are disposed so as to intersect with one optical axis.

Figure 14:
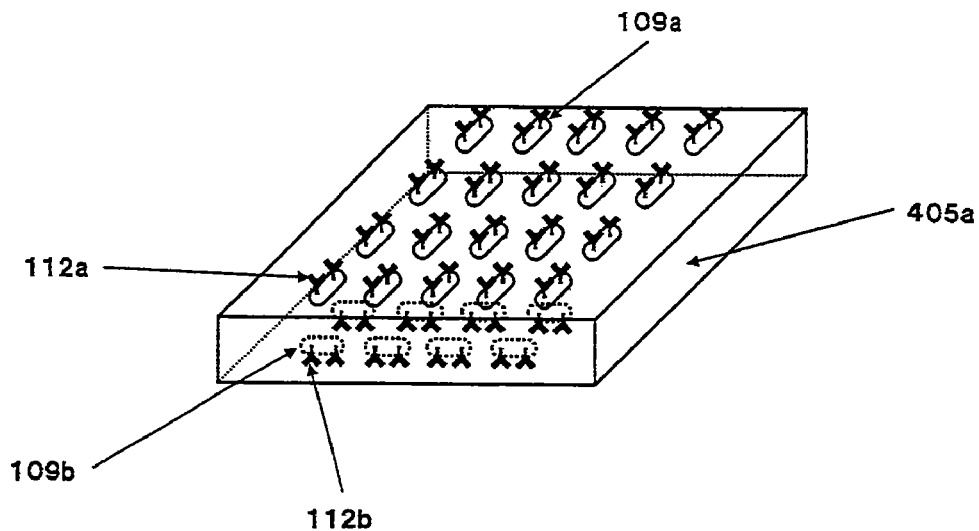
FIG. 14 schematically illustrates a substrate according to Embodiment 4 of the present invention.

FIG. 14 schematically illustrates the substrate 405a according to the present embodiment. In FIG. 14, the long-axis direction of the first metallic nanorod 109a is orthogonal to the long-axis direction of the second metallic nanorod 109b. The surface of the first metallic nanorod 109a has the first antibody 112a. The surface of the second metallic nanorod 109b has the second antibody 112b.

Figure 15:
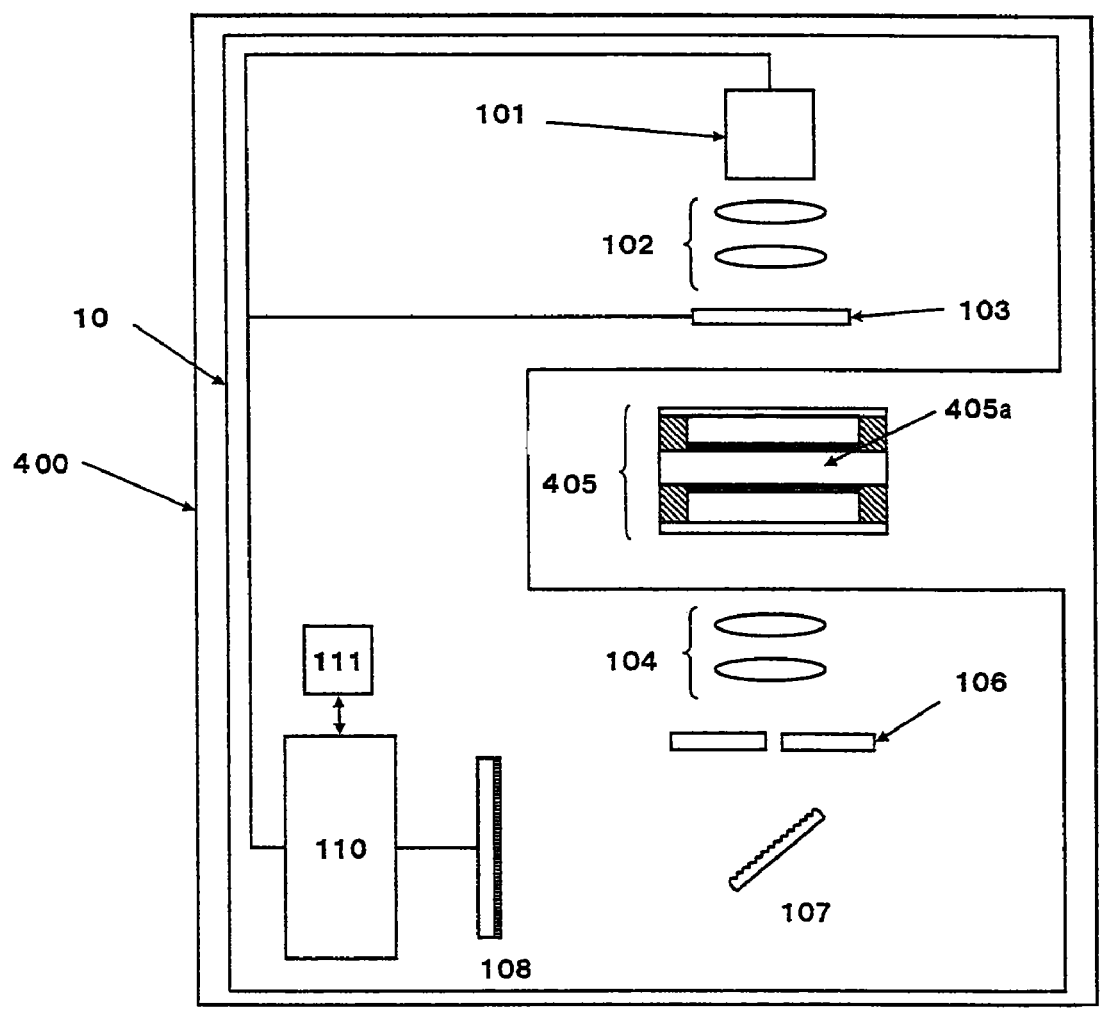
FIG. 15 schematically illustrates the constitution of an apparatus for biogenic substance concentration measurement according to Embodiment 4 of the present invention.

FIG. 15 schematically illustrates the constitution of an apparatus for biogenic substance concentration measurement according to the present embodiment. The biogenic substance concentration measuring apparatus 400 in FIG. 15 has the same constitution as in Embodiment 1, except for comprising the above-described cell 405.

Operation of the apparatus for biogenic substance concentration measurement according to the present embodiment is basically the same as in Embodiment 1. Therefore, explanation will be omitted. In the cell according to the present embodiment, it is not necessary to combine a plurality of substrates each having metallic nanorods immobilized thereon. Therefore, it is not necessary to dispose a plurality of substrates in a manner where the long-axis direction of the first metallic nanorod is orthogonal to the long-axis direction of the second metallic nanorod. Since a plurality of substrates are not used, the cell can be easily, reduced in size. Further, deviations can be suppressed in the respective long-axis directions of the first metallic nanorod 109a and the second metallic nanorod 109b resulting from bonding a plurality of substrates together.

Embodiment 5

A still further embodiment of the present invention will be explained using FIGS. 16A to 17.

Figure 16:
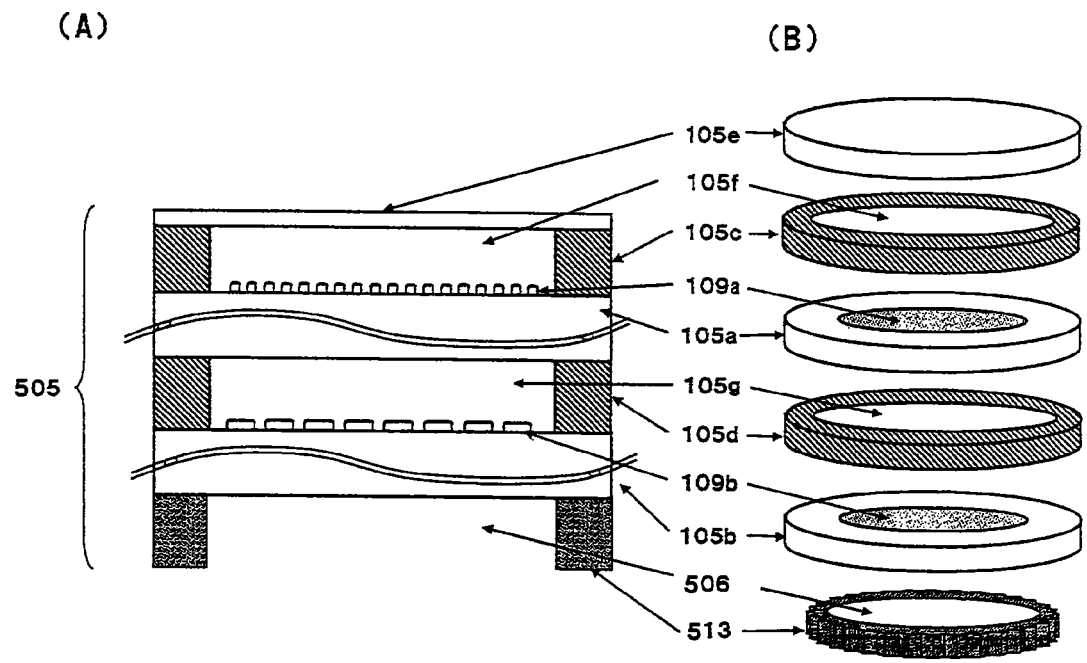
FIG. 16 schematically illustrates the cross section of a cell according to Embodiment 5 of the present invention and an exploded perspective view thereof.
Figure 17:
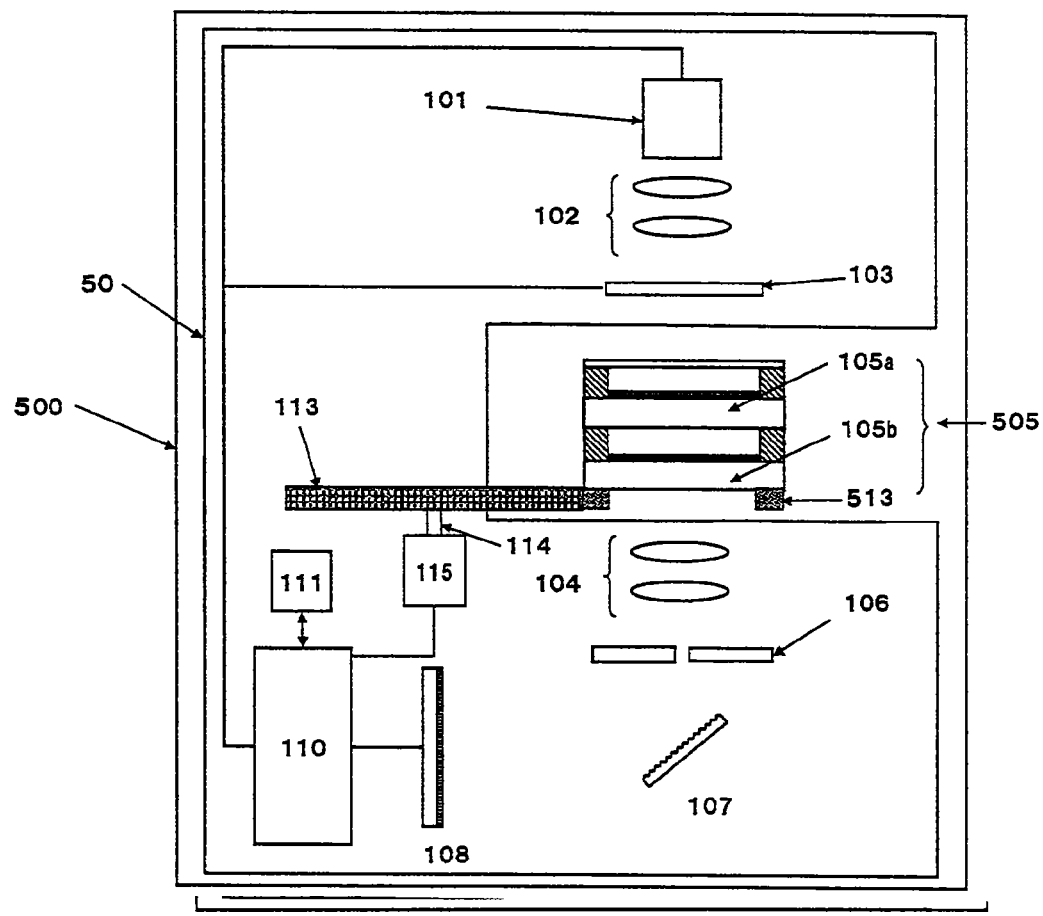
FIG. 17 schematically illustrates the constitution of an apparatus for biogenic substance concentration measurement according to Embodiment 5 of the present invention.

In FIGS. 16 to 17, for the same components as in FIGS. 4 to 6, the same corresponding reference numerals will be used and explanation will be omitted.

FIG. 16 schematically illustrates the cross section and of a cell according to the present embodiment and an exploded perspective view thereof.

The cell 505 according to the present embodiment has basically the same constitution as the cell 105 according to Embodiment 1. The cell 505 comprises a cog-wheel 513 on the face not having the second region of the second substrate 105b. The cog-wheel 513 has near the center thereof a through-hole 506 intersecting with the optical axis. The size of the through-hole 506 is not particularly limited, and is acceptable as long as the light radiated from the light source is not blocked. Thus, the light is transmitted through the cell 505 without being blocked by the cog-wheel 513.

An optical measuring apparatus according to the present embodiment comprises a rotating apparatus for rotating the cell. FIG. 17 schematically illustrates the constitution of the apparatus for biogenic substance concentration measurement according to the present embodiment. The optical measuring apparatus 50 comprises a cog-wheel 113, a shaft 114, and a motor 115. The cog-wheel 113 is in contact with the cog-wheel 513 of the cell 505. This allows the cell 505 to be rotated with an optical axis as the rotation axis. The cog-wheel 113 is connected to the motor 115 via the shaft 114. The motor 115 is connected to the microcomputer 110. The microcomputer 110 controls the motor 115 to run and the cell 505 to rotate.

Although the halogen light source 101 is used in the present embodiment, a light source which radiates polarized light may be used, as in Embodiment 1. In this case, the polarizing plate 103 may not be used.

A biogenic substance concentration measuring apparatus 500 may comprise a photosensor (not illustrated). The photosensor senses the polarized light transmitted through the cell 505 as being parallel to either one of the long-axis direction of the first metallic nanorod 109*a* and the long-axis direction of the second metallic nanorod 109*b*. In this case, the cell 505 preferably comprises projections at the circular outer periphery thereof, so that the cell 505 blocks the light of the photosensor when the polarlized light becomes parallel to either one of the long-axis direction of the first metallic nanorod 109*a* and the long-axis direction of the second metallic nanorod 109*b*. By the projections blocking the light of the photosensor, the polarized light can be sensed as being parallel to the long-axis direction of either one of the metallic nanorods.

Next, operation of the apparatus for biogenic substance concentration measurement of the present embodiment will be explained with reference to drawings.

First, the first wavelength is obtained as in Embodiment 1. At this time, if necessary, the polarized light is set parallel to the long-axis direction of the plurality of first metallic nanorods 109*a*, by rotating the cell 505.

After obtaining the first wavelength, the microcomputer 110 controls the motor 115 to run and the cell 505 to rotate by 90°. This enables the polarized light to be set parallel to the long-axis direction of the plurality of second metallic nanorods 109*b*.

Subsequently, the second wavelength is obtained as in Embodiment 1. This enables the respective concentrations of the first antigen and the second antigen to be calculated.

Although a cell having a constitution similar to that in Embodiment 1 is used in the present embodiment, a cell having a constitution similar to those in Embodiments 2 to 4 may also be used.

INDUSTRIAL APPLICABILITY

The apparatus for biogenic substance concentration measurement according to the present invention is of a small size, and can measure multiple biogenic substance concentrations with high accuracy. Therefore, it is useful when the concentration of a plurality of antigens contained in the test solution is low.

REFERENCE SIGNS LIST

100, 200, 300, 400, 500 biogenic substance concentration measuring apparatus
101 halogen light source
103 polarizing plate
105, 205, 305, 405, 505 cell
105*a* first substrate
105*b* second substrate
105*c*, 305*c*, 405*c* first spacer
105*d*, 305*d*, 405*d* second spacer
105*e* cover glass
105*f*, 305*f*, 405*f* first space
105*g*, 305*g*, 405*g* second space
108 photoreceiver
109*a* first metallic nanorod
109*b* second metallic nanorod
110 microcomputer
112*a* first antibody
112*b* second antibody
113 cog-wheel
114 shaft
115 motor
10, 50 optical measuring apparatus
205*c* spacer
205*f* test solution retention space
506 through-hole
513 cog-wheel
405*a* substrate
305*e*, 405*b* first cover glass
305*h*, 405*e* second cover glass
305*i* third spacer

The invention claimed is:

1. A method for measuring respective concentrations of a first antigen and a second antigen contained in a test solution by using an apparatus for biogenic substance concentration measurement, having the steps of:

preparing said apparatus for biogenic substance concentration measurement, said apparatus comprising:

a cell comprising therein a first region, a second region, and a test solution retention space;

a light source;

a polarizing plate for polarizing light radiated from said light source; and a photoreceiver for receiving light transmitted through said cell along an optical axis intersecting with said first region, said second region, and said test solution retention space, wherein a plurality of first metallic nanorods each having a first antibody on a surface thereof are immobilized on said first region, a plurality of second metallic nanorods each having a second antibody on a surface thereof are immobilized on said second region, the respective long axes of said plurality of first metallic nanorods are aligned in the same direction, the respective long axes of said plurality of second metallic nanorods are aligned in the same direction, the long-axis direction of said first metallic nanorod is orthogonal to the long-axis direction of said second metallic nanorod, and at least one of said polarizing plate and said cell is capable of rotation with said optical axis as the rotation axis, supplying said test solution to said test solution retention space to allow said first antigen and said second antigen to react with said first antibody and said second antibody, respectively, transmitting along said optical axis a polarized light parallel to the long-axis direction of said plurality of first metallic nanorods to receive with said photoreceiver a first light thus obtained, rotating at least one of said polarizing plate and said cell to set a polarized light transmitted through said polarizing plate to be parallel to the long-axis direction of said plurality of second metallic nanorods, transmitting along said optical axis said polarized light parallel to the long-axis direction of said plurality of second metallic nanorods to receive with said photoreceiver a second light thus obtained, and calculating the respective concentrations of said first antigen and said second antigen based respectively on said first light and said second light.

2. The method in accordance with claim 1,
wherein said cell comprises a first substrate and a second substrate,
said first substrate having said first region on one surface thereof, and
said second substrate having said second region on one surface thereof.

3. The method in accordance with claim 2,
wherein said first region and said second region face the same direction.

4. The method in accordance with claim 3,
wherein a first spacer is disposed around said first region,
a cover is disposed correspondingly to said first substrate with said first spacer interposed therebetween,
said first region, said first spacer, and said cover form a first space,
a second spacer is disposed around said second region,
the other face of said first substrate, said second region, and said second spacer form a second space, and
said first space and said second space form said test solution retention space.

5. The method in accordance with claim 2,
wherein said first region and said second region face each other.

6. The method in accordance with claim 5,
wherein a spacer is disposed around said first region or around said second region, and
said first region, said second region, and said spacer form said test solution retention space.

7. The method in accordance with claim 2,
wherein a first spacer is disposed around said first region,
a first cover is disposed correspondingly to said first substrate with said first spacer interposed therebetween,
said first region, said first spacer, and said first cover form a first space,
a second spacer is disposed around said second region,
a second cover is disposed correspondingly to said second substrate with said second spacer interposed therebetween,
said second region, said second spacer, and said second cover form a second space, and
said first space and said second space form said test solution retention space.

8. The method in accordance with claim 1,
wherein said cell comprises a first substrate having said first region on one face thereof and said second region on the other face thereof.

9. The method in accordance with claim 8,
wherein a first spacer is disposed around said first region,
a first cover is disposed correspondingly to said first substrate with said spacer interposed therebetween,
a second spacer is disposed around said second region,
a second cover is disposed correspondingly to said first substrate with said second spacer interposed therebetween,
said first region, said first spacer, and said first cover form a first space,
said second region, said second spacer, and said second cover form a second space, and
said first space and said second space form said test solution retention space.

10. A method for measuring respective concentrations of a first antigen and a second antigen contained in a test solution by using an apparatus for biogenic substance concentration measurement, having the steps of:
preparing said apparatus for biogenic substance concentration measurement,
said apparatus comprising:
a cell comprising therein a first region, a second region, and a test solution retention space;
a light source for radiating polarized light to said cell; and
a photoreceiver for receiving light transmitted through said cell along an optical axis intersecting with said first region, said second region, and said test solution retention space,
wherein a plurality of first metallic nanorods each having a first antibody on a surface thereof are immobilized on said first region,
a plurality of second metallic nanorods each having a second antibody on a surface thereof are immobilized on said second region,
the respective long axes of said plurality of first metallic nanorods are aligned in the same direction,
the respective long axes of said plurality of second metallic nanorods are aligned in the same direction,
the long-axis direction of said first metallic nanorod is orthogonal to the long-axis direction of said second metallic nanorod, and
at least one of said light source and said cell is capable of rotation with said optical axis as the rotation axis,
supplying said test solution to said test solution retention space to allow said first antigen and said second antigen to react with said first antibody and said second antibody, respectively,
transmitting along said optical axis a polarized light parallel to the long-axis direction of said plurality of first metallic nanorods to receive with said photoreceiver a first light thus obtained,
rotating at least one of said light source and said cell to set a polarized light radiated from said light source to be parallel to the long-axis direction of said plurality of second metallic nanorods,
transmitting along said optical axis said polarized light parallel to the long-axis direction of said plurality of second metallic nanorods to receive with said photoreceiver a second light thus obtained, and
calculating the respective concentrations of said first antigen and said second antigen based respectively on said first light and said second light.

11. The method in accordance with claim 10,
wherein said cell comprises a first substrate and a second substrate,
said first substrate having said first region on one surface thereof, and
said second substrate having said second region on one surface thereof.

12. The method in accordance with claim 11,
wherein said first region and said second region face the same direction.

13. The method in accordance with claim 12,
wherein a first spacer is disposed around said first region,
a cover is disposed correspondingly to said first substrate with said first spacer interposed therebetween,
said first region, said first spacer, and said cover form a first space,
a second spacer is disposed around said second region,
the other face of said first substrate, said second region, and said second spacer form a second space, and said first space and said second space form said test solution retention space.

14. The method in accordance with claim 11, wherein said first region and said second region face each other.

15. The method in accordance with claim 14, wherein a spacer is disposed around said first region or around said second region, and
said first region, said second region, and said spacer form said test solution retention space.

16. The method in accordance with claim 11, wherein a first spacer is disposed around said first region,
a first cover is disposed correspondingly to said first substrate with said first spacer interposed therebetween,
said first region, said first spacer, and said first cover form a first space,
a second spacer is disposed around said second region,
a second cover is disposed correspondingly to said second substrate with said second spacer interposed therebetween,
said second region, said second spacer, and said second cover form a second space, and
said first space and said second space form said test solution retention space.

17. The method in accordance with claim 10, wherein said cell comprises a first substrate having said first region on one face thereof and said second region on the other face thereof.

18. The method in accordance with claim 17, wherein a first spacer is disposed around said first region,
a first cover is disposed correspondingly to said first substrate with said spacer interposed therebetween,
a second spacer is disposed around said second region,
a second cover is disposed correspondingly to said first substrate with said second spacer interposed therebetween,
said first region, said first spacer, and said first cover form a first space,
said second region, said second spacer, and said second cover form a second space, and
said first space and said second space form said test solution retention space.

19. A method for measuring respective concentrations of a first antigen and a second antigen contained in a test solution by using a cell, having the steps of:
preparing said cell,
said cell comprising therein a first region, a second region, and a test solution retention space;
wherein a plurality of first metallic nanorods each having a first antibody on a surface thereof are immobilized on said first region,
a plurality of second metallic nanorods each having a second antibody on a surface thereof are immobilized on said second region,
the respective long axes of said plurality of first metallic nanorods are aligned in the same direction,
the respective long axes of said plurality of second metallic nanorods are aligned in the same direction, and
the long-axis direction of said first metallic nanorod is orthogonal to the long-axis direction of said second metallic nanorod;
supplying said test solution to said test solution retention space to allow said first antigen and said second antigen to react with said first antibody and said second antibody, respectively;
transmitting through said cell along an optical axis intersecting with said first region, said second region, and said test solution retention space, a polarized light parallel to the long-axis direction of said plurality of first metallic nanorods to obtain a first light;
transmitting through said cell along said optical axis, a polarized light parallel to the long-axis direction of said plurality of second metallic nanorods to obtain a second light; and
calculating the respective concentrations of said first antigen and said second antigen based respectively on said first light and said second light.

20. The method in accordance with claim 19, wherein said cell comprises a first substrate and a second substrate,
said first substrate having said first region on one surface thereof, and
said second substrate having said second region on one surface thereof.

21. The method in accordance with claim 20, wherein said first region and said second region face the same direction.

22. The method in accordance with claim 21, wherein a first spacer is disposed around said first region,
a cover is disposed correspondingly to said first substrate with said first spacer interposed therebetween,
said first region, said first spacer, and said cover form a first space,
a second spacer is disposed around said second region,
the other face of said first substrate, said second region, and said second spacer form a second space, and
said first space and said second space form said test solution retention space.

23. The method in accordance with claim 20, wherein said first region and said second region face each other.

24. The method in accordance with claim 23, wherein a spacer is disposed around said first region or around said second region, and
said first region, said second region, and said spacer form said test solution retention space.

25. The method in accordance with claim 20, wherein a first spacer is disposed around said first region,
a first cover is disposed correspondingly to said first substrate with said first spacer interposed therebetween,
said first region, said first spacer, and said first cover form a first space,
a second spacer is disposed around said second region,
a second cover is disposed correspondingly to said second substrate with said second spacer interposed therebetween,
said second region, said second spacer, and said second cover form a second space, and
said first space and said second space form said test solution retention space.

26. The method in accordance with claim 19, wherein said cell comprises a first substrate having said first region on one face thereof and said second region on the other face thereof.

27. The method in accordance with claim 26, wherein a first spacer is disposed around said first region,
a first cover is disposed correspondingly to said first substrate with said first spacer interposed therebetween,
a second spacer is disposed around said second region,
a second cover is disposed correspondingly to said first substrate with said second spacer interposed therebetween,
said first region, said first spacer, and said first cover form a first space, said second region, said second spacer, and said second cover form a second space, and said first space and said second space form said test solution retention space.

28. An apparatus for biogenic substance concentration measurement, comprising:

a cell comprising therein a first region, a second region, and a test solution retention space;

a light source;

a polarizing plate for polarizing light radiated from said light source; and a photoreceiver for receiving light transmitted through said cell along an optical axis intersecting with said first region, said second region, and said test solution retention space, wherein a plurality of first metallic nanorods each having a first antibody on a surface thereof are immobilized on said first region, a plurality of second metallic nanorods each having a second antibody on a surface thereof are immobilized on said second region, the respective long axes of said plurality of first metallic nanorods are aligned in the same direction, the respective long axes of said plurality of second metallic nanorods are aligned in the same direction, the long-axis direction of said first metallic nanorod is orthogonal to the long-axis direction of said second metallic nanorod, and at least one of said polarizing plate and said cell is capable of rotation with said optical axis as the rotation axis.

29. The apparatus for biogenic substance concentration measurement in accordance with claim 28, wherein said cell comprises a first substrate and a second substrate, said first substrate having said first region on one surface thereof, and said second substrate having said second region on one surface thereof.

30. The apparatus for biogenic substance concentration measurement in accordance with claim 29, wherein said first region and said second region face the same direction.

31. The apparatus for biogenic substance concentration measurement in accordance with claim 30, wherein a first spacer is disposed around said first region, a cover is disposed correspondingly to said first substrate with said first spacer interposed therebetween, said first region, said first spacer, and said cover form a first space, a second spacer is disposed around said second region, the other face of said first substrate, said second region, and said second spacer form a second space, and said first space and said second space form said test solution retention space.

32. The apparatus for biogenic substance concentration measurement in accordance with claim 29, wherein said first region and said second region face each other.

33. The apparatus for biogenic substance concentration measurement in accordance with claim 32, wherein a spacer is disposed around said first region or around said second region, and said first region, said second region, and said spacer form said test solution retention space.

34. The apparatus for biogenic substance concentration measurement in accordance with claim 29, wherein a first spacer is disposed around said first region, a first cover is disposed correspondingly to said first substrate with said first spacer interposed therebetween, said first region, said first spacer, and said first cover form a first space, a second spacer is disposed around said second region, a second cover is disposed correspondingly to said second substrate with said second spacer interposed therebetween, said second region, said second spacer, and said second cover form a second space, and said first space and said second space form said test solution retention space.

35. The apparatus for biogenic substance concentration measurement in accordance with claim 28, wherein said cell comprises a first substrate having said first region on one face thereof and said second region on the other face thereof.

36. The apparatus for biogenic substance concentration measurement in accordance with claim 35, wherein a first spacer is disposed around said first region, a first cover is disposed correspondingly to said first substrate with said first spacer interposed therebetween, a second spacer is disposed around said second region, a second cover is disposed correspondingly to said first substrate with said second spacer interposed therebetween, said first region, said first spacer, and said first cover form a first space, said second region, said second spacer, and said second cover form a second space, and said first space and said second space form said test solution retention space.

37. An apparatus for biogenic substance concentration measurement, comprising:

a cell comprising therein a first region, a second region, and a test solution retention space;

a light source for radiating polarized light to said cell; and a photoreceiver for receiving light transmitted through said cell along an optical axis intersecting with said first region, said second region, and said test solution retention space, wherein a plurality of first metallic nanorods each having a first antibody on a surface thereof are immobilized on said first region, a plurality of second metallic nanorods each having a second antibody on a surface thereof are immobilized on said second region, the respective long axes of said plurality of first metallic nanorods are aligned in the same direction, the respective long axes of said plurality of second metallic nanorods are aligned in the same direction, the long-axis direction of said first metallic nanorod is orthogonal to the long-axis direction of said second metallic nanorod, and at least one of said light source and said cell is capable of rotation with said optical axis as the rotation axis.

38. The apparatus for biogenic substance concentration measurement in accordance with claim 37, wherein said cell comprises a first substrate and a second substrate, said first substrate having said first region on one surface thereof, and said second substrate having said second region on one surface thereof.

39. The apparatus for biogenic substance concentration measurement in accordance with claim 38, wherein said first region and said second region face the same direction.

40. The apparatus for biogenic substance concentration measurement in accordance with claim 39,
wherein a first spacer is disposed around said first region,
a cover is disposed correspondingly to said first substrate with said first spacer interposed therebetween,
said first region, said first spacer, and said cover form a first space,
a second spacer is disposed around said second region,
the other face of said first substrate, said second region, and said second spacer form a second space, and
said first space and said second space form said test solution retention space.

41. The apparatus for biogenic substance concentration measurement in accordance with claim 38,
wherein said first region and said second region face each other.

42. The apparatus for biogenic substance concentration measurement in accordance with claim 41,
wherein a spacer is disposed around said first region or around said second region, and
said first region, said second region, and said spacer form said test solution retention space.

43. The apparatus for biogenic substance concentration measurement in accordance with claim 38,
wherein a first spacer is disposed around said first region,
a first cover is disposed correspondingly to said first substrate with said first spacer interposed therebetween,
said first region, said first spacer, and said first cover form a first space,
a second spacer is disposed around said second region,
a second cover is disposed correspondingly to said second substrate with said second spacer interposed therebetween,
said second region, said second spacer, and said second cover form a second space, and
said first space and said second space form said test solution retention space.

44. The apparatus for biogenic substance concentration measurement in accordance with claim 37,
wherein said cell comprises a first substrate having said first region on one face thereof and said second region on the other face thereof.

45. The apparatus for biogenic substance concentration measurement in accordance with claim 44,
wherein a first spacer is disposed around said first region,
a first cover is disposed correspondingly to said first substrate with said spacer interposed therebetween,
a second spacer is disposed around said second region,
a second cover is disposed correspondingly to said first substrate with said second spacer interposed therebetween,
said first region, said first spacer, and said first cover form a first space,
said second region, said second spacer, and said second cover form a second space, and
said first space and said second space form said test solution retention space.

* * * * *